(12) United States Patent
Everett et al.

(10) Patent No.: US 6,437,214 B1
(45) Date of Patent: Aug. 20, 2002

(54) LAYERED ABSORBENT STRUCTURE WITH A ZONED BASIS WEIGHT AND A HETEROGENEOUS LAYER REGION

(75) Inventors: Rob David Everett; Thomas Gerald Bolwerk; Richard Norris Dodge, II, all of Appleton; Violet May Grube, Greenville; Yong Li, Appleton; Debra Jean McDowall, Neenah; Shannon Kathleen Melius, Appleton; Lawrence Howell Sawyer; David Louis Zenker, both of Neenah; Xiaomin Zhang, Appleton, all of WI (US); Sylvia Bandy Little, Marietta, GA (US); Billie Jean Matthews, Woodstock, GA (US); Sridhar Ranganathan, Suwanee, GA (US); Stanley Michael Gryskiewicz, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/478,686

(22) Filed: Jan. 6, 2000

(51) Int. Cl.$^7$ ................................................ A61F 13/15
(52) U.S. Cl. ........................................................ 604/378
(58) Field of Search ................................. 604/378, 379

(56) References Cited

U.S. PATENT DOCUMENTS 3,670,731 A  6/1972  Harmon (List continued on next page.)

FOREIGN PATENT DOCUMENTS

EP          0 217 032 A2    4/1987

(List continued on next page.)

OTHER PUBLICATIONS

American Society for Testing Materials (ASTM) Designation: E 11–87, "Standard Specification for Wire–Cloth Sieves," pp. 13–16, published Jul. 1987.

(List continued on next page.)

*Primary Examiner*—John J. Calvert
*Assistant Examiner*—Angela J. Grayson
(74) *Attorney, Agent, or Firm*—Paul Yee

(57) ABSTRACT

A distinctive absorbent article includes an absorbent core having multiple absorbent layers, wherein the absorbent layers interact in such a manner which preferentially locates absorbed liquid in an appointed, high saturation wicking layer. The localization of the liquid within this wicking layer increases the potential of this layer to move liquid through capillary action due to the higher saturation level and increased amount of liquid available. The intake capability of the absorbent system is maintained or improved over current systems by keeping a second layer of the absorbent system at low saturation levels through as many insults of the product as possible, while providing optimum intake performance through appropriate control of the composite properties. The low saturation in this layer provides void volume for the incoming insult as well, as a high permeability, thus increasing the intake rate of the absorbent system as a whole, but the structure of the low saturation layer is also balanced to provide an appropriately high level of capillary tension to provide enough control of the liquid to stop leakage from occurring. This low saturation layer is used in addition to a surge material and provides intake functionality in addition to that provided by the surge material. In particular aspects of the invention, the body side layer of the absorbent core does not extend over the entire surface of the overall absorbent core, therefore is not used as the high saturation, wicking layer, but as the intake layer. This arrangement also allows the intake layer to be in direct contact with the incoming liquid, therefore allowing for more immediate access and improved intake function. In additional aspects, at least one primary layer region can have a non-uniform, selectively zoned basis weight distribution. Particular configurations of the at least one primary layer region can be constructed with a target area of such primary layer region having a basis weight which is less than a basis weight of another non-target portion of the primary layer region. Moreover, at least one primary layer region can have a heterogeneous structure. In particular constructions, the at least one primary layer region can include a plurality of two or more sublayers.

22 Claims, 16 Drawing Sheets

U.S. PATENT DOCUMENTS

| | | |
|---|---|---|
| 3,888,256 A | 6/1975 | Studinger |
| 3,901,236 A | 8/1975 | Assarsson et al. |
| 4,047,531 A | 9/1977 | Karami |
| 4,055,180 A | 10/1977 | Karami |
| 4,055,184 A | 10/1977 | Karami |
| 4,076,663 A | 2/1978 | Masuda et al. |
| 4,102,340 A | 7/1978 | Mesek et al. |
| 4,103,062 A | 7/1978 | Aberson et al. |
| 4,145,464 A | 3/1979 | McConnell et al. |
| 4,186,165 A | 1/1980 | Aberson et al. |
| 4,212,302 A | 7/1980 | Karami |
| 4,269,188 A | 5/1981 | Nishizawa et al. |
| 4,286,082 A | 8/1981 | Tsubakimoto et al. |
| 4,338,371 A | 7/1982 | Dawn et al. |
| 4,411,660 A | 10/1983 | Dawn et al. |
| 4,500,315 A | 2/1985 | Pieniak et al. |
| 4,531,945 A | 7/1985 | Allison |
| 4,537,590 A | 8/1985 | Pieniak et al. |
| 4,540,454 A | 9/1985 | Pieniak et al. |
| 4,573,988 A | 3/1986 | Pieniak et al. |
| 4,578,068 A | 3/1986 | Kramer et al. |
| 4,590,114 A | 5/1986 | Holtman |
| 4,600,458 A | 7/1986 | Kramer et al. |
| 4,610,678 A | 9/1986 | Weisman et al. |
| 4,663,220 A | 5/1987 | Wisneski et al. |
| 4,673,402 A | 6/1987 | Weisman et al. |
| 4,699,823 A | 10/1987 | Kellenberger et al. |
| 4,704,116 A | 11/1987 | Enloe |
| 4,753,646 A | 6/1988 | Enloe |
| 4,806,408 A | 2/1989 | Pierre et al. |
| 4,822,453 A | 4/1989 | Dean et al. |
| 4,842,594 A | 6/1989 | Ness |
| 4,880,419 A | 11/1989 | Ness |
| 4,888,231 A | 12/1989 | Angstadt |
| 4,898,642 A | 2/1990 | Moore et al. |
| 4,908,175 A | 3/1990 | Angstadt |
| 4,916,005 A | 4/1990 | Lippert et al. |
| 4,927,582 A | 5/1990 | Bryson |
| 4,935,022 A | 6/1990 | Lash et al. |
| 4,938,753 A | 7/1990 | Van Gompel et al. |
| 5,009,650 A | 4/1991 | Bernardin |
| 5,013,309 A | 5/1991 | Baigas, Jr. et al. |
| 5,019,063 A | 5/1991 | Marsan et al. |
| 5,019,073 A | 5/1991 | Roessler et al. |
| 5,043,206 A | 8/1991 | Ternstrom |
| 5,061,259 A | 10/1991 | Goldman et al. |
| 5,100,397 A | 3/1992 | Poccia et al. |
| 5,124,197 A | 6/1992 | Bernardin et al. |
| 5,145,727 A | 9/1992 | Potts et al. |
| 5,149,335 A | 9/1992 | Kellenberger et al. |
| 5,156,902 A | 10/1992 | Pieper et al. |
| 5,171,237 A | 12/1992 | Poccia et al. |
| 5,217,445 A | 6/1993 | Young et al. |
| 5,226,992 A | 7/1993 | Morman |
| 5,231,222 A | 7/1993 | Palumbo et al. |
| 5,246,429 A | 9/1993 | Poccia et al. |
| 5,248,524 A | 9/1993 | Soderlund |
| 5,262,223 A | 11/1993 | Palumbo et al. |
| 5,281,207 A | 1/1994 | Chmielewski et al. |
| 5,300,054 A | 4/1994 | Feist et al. |
| 5,304,161 A | 4/1994 | Noel et al. |
| 5,330,822 A | 7/1994 | Berg et al. |
| 5,348,547 A | 9/1994 | Payne et al. |
| 5,350,370 A | 9/1994 | Jackson et al. |
| 5,356,403 A | 10/1994 | Faulks et al. |
| 5,360,420 A | 11/1994 | Cook et al. |
| 5,364,382 A | 11/1994 | Latimer et al. |
| 5,399,219 A | 3/1995 | Roessler et al. |
| 5,439,458 A | 8/1995 | Noel et al. |
| 5,447,677 A | 9/1995 | Griffoul et al. |
| 5,460,622 A | 10/1995 | Dragoo et al. |
| 5,482,761 A | 1/1996 | Palumbo et al. |
| 5,486,166 A | 1/1996 | Bishop et al. |
| 5,486,167 A | 1/1996 | Dragoo et al. |
| 5,490,846 A | 2/1996 | Ellis et al. |
| 5,505,718 A | 4/1996 | Roe et al. |
| 5,505,719 A | 4/1996 | Cohen et al. |
| 5,520,673 A | 5/1996 | Yarbrough et al. |
| 5,525,407 A | 6/1996 | Yang |
| 5,531,728 A | 7/1996 | Lash |
| 5,540,796 A | 7/1996 | Fries |
| 5,550,189 A | 8/1996 | Qin et al. |
| 5,558,655 A | 9/1996 | Jezzi et al. |
| 5,562,645 A | 10/1996 | Tanzer et al. |
| 5,562,646 A | 10/1996 | Goldman et al. |
| 5,562,650 A | 10/1996 | Everett et al. |
| 5,569,226 A | 10/1996 | Cohen et al. |
| 5,593,399 A | 1/1997 | Tanzer et al. |
| 5,595,618 A | 1/1997 | Fries et al. |
| 5,599,335 A | 2/1997 | Goldman et al. |
| 5,599,336 A | 2/1997 | Plischke |
| 5,601,542 A | 2/1997 | Melius et al. |
| 5,605,735 A | 2/1997 | Zehner et al. |
| 5,614,570 A | 3/1997 | Hansen et al. |
| 5,624,429 A | 4/1997 | Long et al. |
| 5,629,377 A | 5/1997 | Burgert et al. |
| 5,649,915 A | 7/1997 | Chauvette et al. |
| 5,653,702 A | 8/1997 | Brohammer et al. |
| 5,669,894 A | 9/1997 | Goldman et al. |
| 5,681,300 A | 10/1997 | Ahr et al. |
| 5,714,156 A | 2/1998 | Schmidt et al. |
| 5,720,736 A | 2/1998 | Hatsuda et al. |
| 5,720,737 A | 2/1998 | Hamajima et al. |
| 5,728,082 A | 3/1998 | Gustafsson et al. |
| 5,728,084 A | 3/1998 | Palumbo et al. |
| 5,730,737 A | 3/1998 | Widlund et al. |
| 5,741,241 A | 4/1998 | Guidotti et al. |
| 5,762,641 A | 6/1998 | Bewick-Sonntag et al. |
| 5,762,844 A | 6/1998 | Van Himbergen et al. |
| 5,779,860 A | 7/1998 | Hollenberg et al. |
| 5,785,696 A | 7/1998 | Inoue et al. |
| 5,788,684 A | 8/1998 | Abuto et al. |
| 5,797,894 A | 8/1998 | Cadieux et al. |
| 5,800,417 A | 9/1998 | Georg-Wood et al. |
| 5,800,418 A | 9/1998 | Ahr |
| 5,800,419 A | 9/1998 | Soga et al. |
| 5,807,362 A | 9/1998 | Serbiak et al. |
| 5,814,034 A | 9/1998 | Widlund et al. |
| 5,817,081 A | 10/1998 | La Von et al. |
| 5,817,085 A | 10/1998 | Widlund et al. |
| 5,820,973 A | 10/1998 | Dodge, II et al. |
| 5,830,202 A | 11/1998 | Bogdanski et al. |
| 5,836,929 A | 11/1998 | Bewick-Sonntag et al. |
| 5,843,061 A | 12/1998 | Chauvette et al. |
| 5,843,063 A | 12/1998 | Anderson et al. |
| 5,843,852 A | 12/1998 | Dutkiewicz et al. |
| 5,849,002 A | 12/1998 | Carlos et al. |
| 5,853,867 A | 12/1998 | Harada et al. |
| 5,855,571 A | 1/1999 | Steger et al. |
| 5,877,097 A | 3/1999 | West et al. |
| 5,882,464 A | 3/1999 | Theisgen et al. |
| 5,891,119 A | 4/1999 | Ta et al. |
| 5,891,120 A | 4/1999 | Chmielewski |
| 5,895,379 A | 4/1999 | Litchholt et al. |
| 5,904,675 A | 5/1999 | Laux et al. |
| 5,961,506 A | 10/1999 | Guidotti et al. |
| 6,030,373 A | 2/2000 | VanGompel et al. |

FOREIGN PATENT DOCUMENTS

| | | |
|---|---|---|
| EP | 0 558 889 A1 | 9/1993 |
| EP | 0 343 941 B1 | 4/1994 |

| | | |
|---|---|---|
| EP | 0 325 416 B1 | 5/1994 |
| EP | 0 615 736 A1 | 9/1994 |
| EP | 0 631 768 A1 | 1/1995 |
| EP | 0 640 330 A1 | 3/1995 |
| EP | 0 592 401 B1 | 8/1995 |
| EP | 0 689 815 A1 | 1/1996 |
| EP | 0 691 133 A1 | 1/1996 |
| EP | 0 692 231 A1 | 1/1996 |
| EP | 0 695 541 A1 | 2/1996 |
| EP | 0 697 217 A1 | 2/1996 |
| EP | 0 700 672 A1 | 3/1996 |
| EP | 0 700 673 A1 | 3/1996 |
| EP | 0 401 189 B2 | 6/1996 |
| EP | 0 523 744 B1 | 10/1996 |
| EP | 0 512 001 B1 | 5/1997 |
| EP | 0 758 219 B1 | 8/1998 |
| EP | 0 875 225 A1 | 11/1998 |
| EP | 0 637 953 B1 | 1/1999 |
| EP | 0 726 752 B1 | 4/1999 |
| EP | 0 933 074 A1 | 8/1999 |
| EP | 0 661 030 B1 | 7/2000 |
| FR | 2 627 080 A1 | 4/1989 |
| GB | 2 280 115 A | 1/1995 |
| GB | 2 296 511 A | 7/1996 |
| WO | WO 90/14815 A1 | 12/1990 |
| WO | WO 91/15177 A1 | 10/1991 |
| WO | WO 95/17870 A1 | 7/1995 |
| WO | WO 97/13484 A1 | 4/1997 |
| WO | WO 97/17924 A1 | 5/1997 |
| WO | WO 97/23184 A1 | 7/1997 |
| WO | WO 98/14151 A1 | 4/1998 |
| WO | WO 98/22059 A1 | 5/1998 |
| WO | WO 98/22065 A1 | 5/1998 |
| WO | WO 98/22067 A1 | 5/1998 |
| WO | WO 98/24621 A1 | 6/1998 |
| WO | WO 99/32165 A1 | 7/1999 |

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

TAPPI Official Test Method T 543 om–94, "Bending Resistance of Paper (Gurley Type Tester)," published by the TAPPI Press, Atlanta, Georgia, pp. 1–7.

Berdichevsky, A.L. and Zhong Cai, "Preform Permeability Predictions by Self–Consistent Method and Finite Element Simulation," *Polymer Composites,* vol. 14, No. 2, Apr. 1993, pp. 132–143.

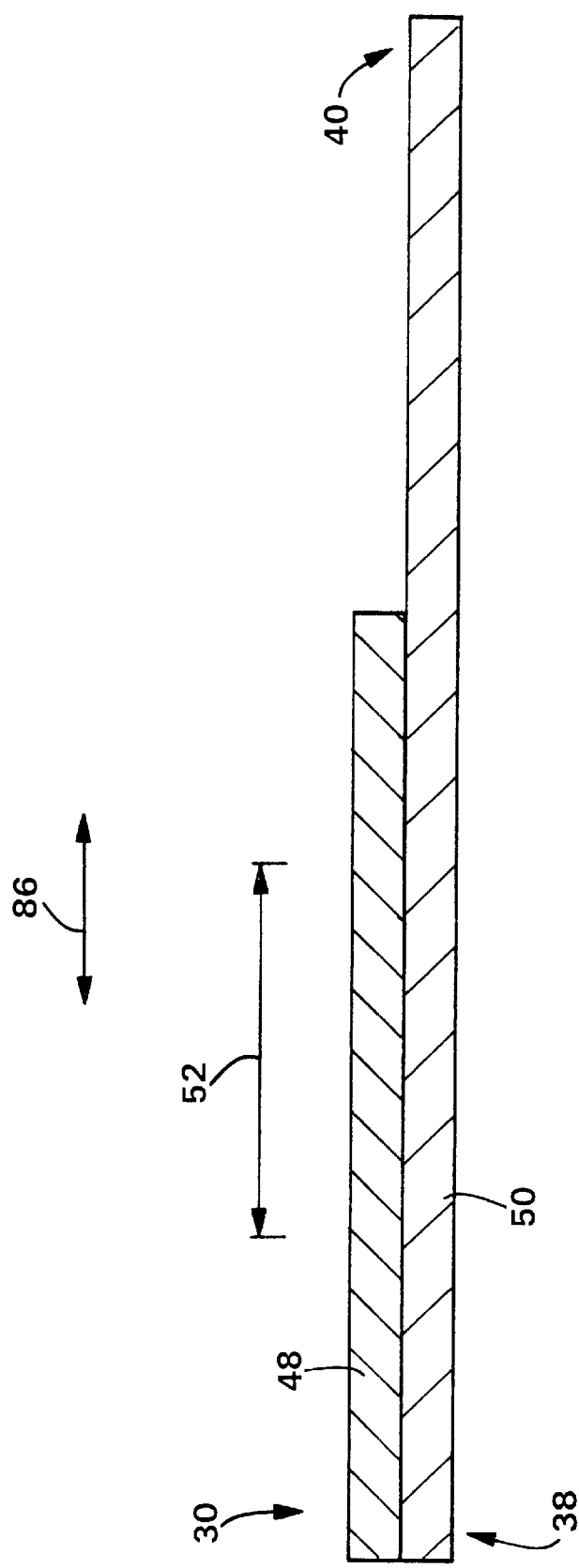

LAYERED ABSORBENT STRUCTURE WITH A ZONED BASIS WEIGHT AND A HETEROGENEOUS LAYER REGION

FIELD OF THE INVENTION

The present invention relates to a layered absorbent structure. More particularly, the invention relates to a layered, composite absorbent structure with individual layers which are constructed and arranged to selectively cooperate to provide desired performance parameters in the composite, layered structure.

BACKGROUND OF THE INVENTION

Performance objectives of disposable absorbent articles, such as infant diapers, include no product leakage, dry feel to the wearer, and a comfortable fit throughout the product life. Accordingly, absorbent articles typically contain an absorbent core to provide liquid handling and other absorbent functionalities required to meet the product performance objectives. The absorbent core of absorbent articles is commonly composed of wood pulp fibers, and superabsorbent material is often distributed in the absorbent core to enhance the liquid absorbent capacity. The absorbent core is usually formed in an hourglass, T-shaped, or similar configuration with reduced absorbent width in the central crotch region for wearer fit and comfort.

Absorbent articles frequently leak before the liquid absorbent capacity of the entire absorbent core is fully utilized. One problem resulting in leakage is the inability of the absorbent core to fully uptake liquids rapidly and completely when large amounts of liquids are discharged into the absorbent article. Another associated problem contributing to leakage is the inability of the absorbent core to move or distribute sufficient amounts of liquid between discharges from a target area portion of the absorbent article to more distal and more remote end regions of the absorbent core which have not been utilized. This results in saturation of only the central target area of the absorbent core and excessive thickness, bulkiness, and sagging of the wet, heavy absorbent material resulting in poor performance, product fit and wearer discomfort. These absorbent core deficiencies are especially acute for thin, narrower-crotch absorbent designs having a crotch width of less than about 4 inches that provides less absorbent mass and bulk in the target area for improved product fit.

The absorbent core of current absorbent articles does not adequately meet current performance objectives. The desirable absorbent core liquid uptake and distribution functionalities required for upstream narrower crotch higher efficiency absorbent article designs is also beyond current capabilities. Consequently, there remains a need for absorbent structures which can provide improved fluid uptake of liquid insults and improved liquid distribution to move liquid out of the target area between liquid insults to maintain this desirable liquid uptake behavior for the life of the product.

BRIEF DESCRIPTION OF THE INVENTION

The disclosed invention is an absorbent system which includes multiple absorbent layer regions. The two or more absorbent layer regions can advantageously interact in a manner which preferentially locates an appointed liquid in a selected layer region. This localization of the liquid within this layer region can increase the potential of this layer region to move liquid through capillary action due to the higher saturation level and increased amount of liquid available. The intake capability of the absorbent system can be maintained or improved over current systems by keeping a layer region of the absorbent system at low saturation levels through as many insults of the product as possible, while providing optimum intake performance through appropriate control of the composite properties. The low saturation in this layer region provides void volume for the incoming insult as well as a high permeability, thus increasing the intake rate of the absorbent system as a whole. The properties of this layer region can advantageously be balanced with an appropriately high level of capillary tension to provide enough control of the liquid to substantially stop undesired leakage. This low saturation layer region can be used in addition to a layer of surge management material and can provide an intake functionality in addition to that provided by the surge material. In particular aspects of the invention, a body side layer of the absorbent structure may not extend over the entire surface of the absorbent system, and may be configured to provide an intake layer portion which is additional to the high saturation, wicking layer region. This arrangement can locate the intake layer region to be in a substantially direct contact with the incoming liquid, and thereby allow a more immediate access to the incoming liquid and an improved, liquid intake function.

In additional aspects, at least one primary layer region can have a non-uniform, selectively zoned basis weight distribution. Particular configurations of the at least one primary layer region can be constructed with a target area of the primary layer region having a basis weight which is less than a basis weight of another non-target portion of the primary layer region. Moreover, at least one primary layer region can have a heterogeneous structure. In particular configurations, the at least one primary layer region can include a plurality of two or more sublayers.

In other aspects of the invention, the layer regions of the absorbent system can cooperate to provide a desired Liquid Wicking Potential value, such as a Liquid Wicking Value of at least about 16%. The invention can also provide a desired Flow Conductance Value, such as a Flow Conductance Value of at least about $7*10^{-6}$ cm$^3$. In additional aspects, the invention can provide a combined Conductance-Wicking value of at least about $14*10^{-6}$ cm$^3$. Further aspects of the invention can provide a system which provides the desired Flow Conductance Value and also includes at least one layer region having the desired Liquid Wicking Value. Still other aspects of the invention can include superabsorbent polymer (SAP) material which exhibits a particular controlled absorbency rate. For example, a desired controlled-rate superabsorbent can exhibit a particular absorbency rate, Tau value, such as a Tau value of at least about 0.67 min. In additional aspects, the invention can include a combination of superabsorbent materials which have a particular ratio of Tau values.

In its various aspects, the present invention can provide an article having a more efficient absorbent structure which is thin with low bulk, has high absorbent capacity, and is resistant to leakage. The configurations of the invention can more fully utilize the total potential absorbent capacity of the absorbent structure, and can more efficiently move and distribute acquired liquid away from the original intake area to more remote areas which are located closer to the distal end regions of the absorbent structure. In addition, the structures of the invention can provide an ability to acquire and intake liquid at a rapid rate, and can maintain the desired intake rate after the absorbent structure has been wetted and has reached a significant portion of its potential, total absorbent capacity.

BRIEF DESCRIPTION OF THE DRAWINGS

The invention will be more fully understood and further advantages will become apparent when reference is made to the following detailed description of the invention and the drawings, in which FIG. 1 representatively shows a top view of an absorbent article which incorporates an absorbent system of the invention;

FIG. 4A representatively shows a longitudinal cross-sectional view of the absorbent core of FIG. 4;

DETAILED DESCRIPTION OF THE INVENTION

Figure 1:
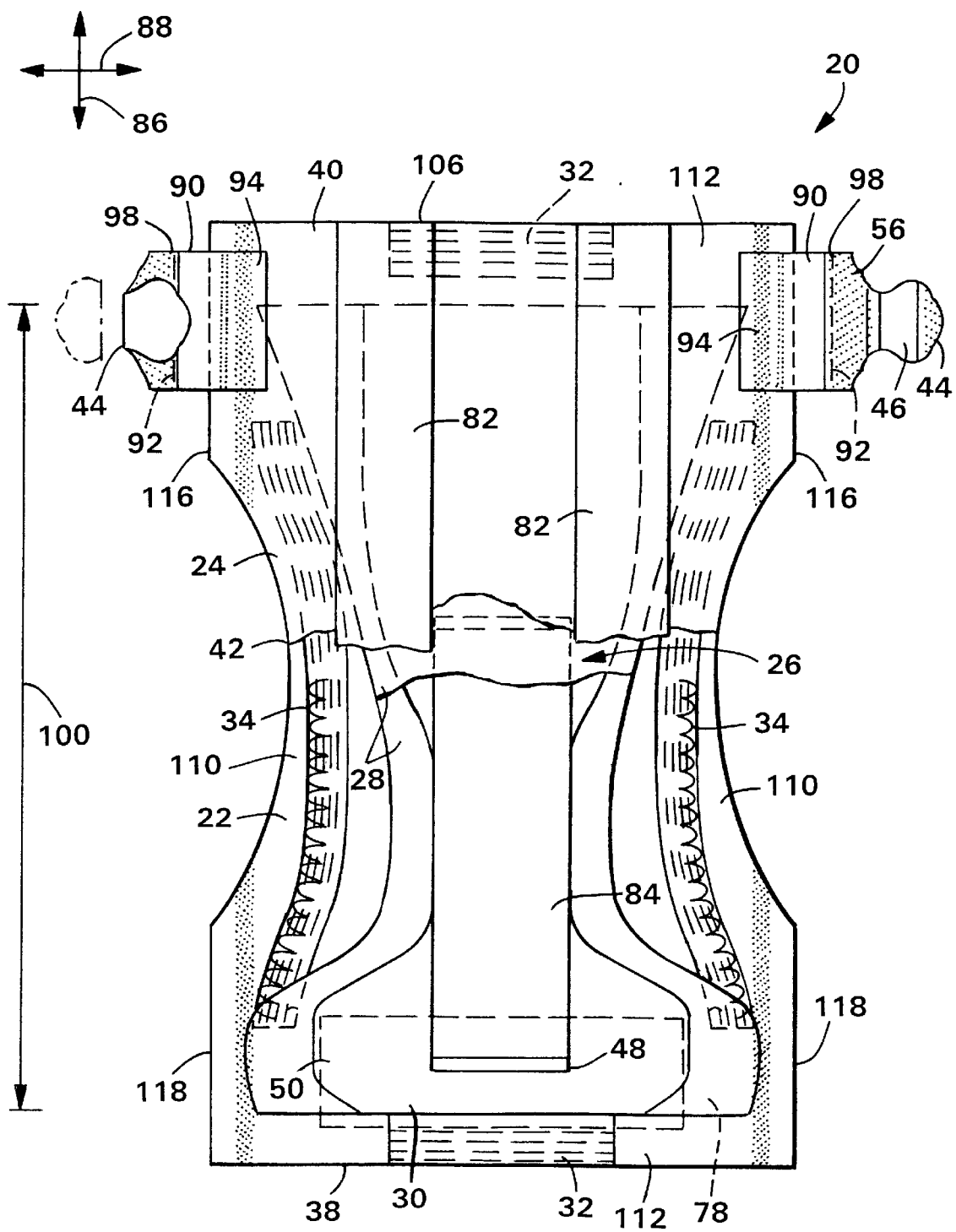
FIG. 1A representatively shows a lateral, cross-sectional view of the article of FIG. 1.
FIG. 1B representatively shows a longitudinal, cross-sectional view of the article of FIG. 1.

The various aspects and embodiments of the invention will be described in the context of a disposable absorbent article, such as a disposable diaper. It is, however, readily apparent that the present invention could also be employed with other articles, such as children's training pants; feminine care articles, incontinence garments, protective cover pads and the like, which may be configured to be disposable. Typically, disposable articles, such as disposable garments, are intended for limited use and are not intended to be laundered or otherwise cleaned for reuse. A disposable diaper, for example, is discarded after it has become soiled by the wearer. In the context of the present invention, a mechanical fastening system is a system which includes cooperating components which mechanically inter-engage to provide a desired securement.

The present invention provides an absorbent system having an absorbent core which includes multiple, layer regions and can provide significantly improved void volume, permeability, and liquid-intake performance in an appointed target region. The absorbent system, particularly an absorbent core portion of the system, can substantially regenerate the desired levels of void volume through a transport of the liquid out of the target region, such as by wicking or other mechanisms. The liquid can advantageously be concentrated in the layer region of the absorbent core which is appointed to provide the desired, relatively high distribution of liquids, while the layer region appointed to provide void volume and intake can remain relatively low in saturation. In most cases the relative basis weights or superabsorbent concentrations of the layer regions can be configured and arranged so that suitably cooperating materials with the appropriate properties will be able to work in the system and provide good performance. It has been found, however, that particular combinations can provide significantly improved performance over others. It should also be noted that the basis weights or other properties of the components may be modified in specific areas of the absorbent structure (e.g.; front vs. back) to optimize cost, other consumer attributes, or to promote desired distributions of the absorbed liquid.

In the present invention, the absorbent layer regions can be distinctively configured to cooperatively interact in a manner which preferentially locates liquid in one or more designated or appointed layer regions. This localization of the liquid within a designated, layer region can increase the potential of this layer region to move and distribute liquid through capillary action, due to the relatively higher saturation level and increased amount of liquid available in the designated layer.

The intake capability of the absorbent system, particularly the intake capability of the absorbent core, can be maintained or improved over conventional systems by keeping a primary, intake layer region of the absorbent system at low saturation levels through as many insults of the product as possible, while providing optimum intake performance through appropriate control of the composite properties. The relatively low level of liquid saturation in this intake layer region provides void volume for the incoming insult as well as a high permeability, thus increasing the intake rate of the absorbent system as a whole. The intake layer region can advantageously be configured to provide an appropriately high level of capillary tension to adequately control of the movement of liquid and substantially avoid undesired leakage. This low saturation, intake layer region is desirably employed in addition to a separately provided surge management portion or layer, and can provide an intake functionality which is additional to that provided by the material of the surge layer.

In particular configurations, the intake layer region can be located on the body side of the absorbent structure, and can be configured to not extend over the entire area expanse of the total, overall absorbent structure. Accordingly, the primary, body side layer region is employed as an intake layer region, and is not employed as the high saturation, wicking layer region. This arrangement also allows the intake layer region to be in a substantially direct contact with the incoming liquid, thereby allowing for a more immediate access to the incoming liquid and a more effective intake function.

The layer regions can be designed, individually or in combination, to provide an improved balance of intake and distribution functions, particularly the intake and distribution of aqueous liquids. The improved performance can, for example, be provided by modifying the physical and/or chemical composition of the component materials or by modifying the physical configurations of the components.

Current fiber and superabsorbent polymer (SAP) composites used in conventional designs of absorbent article, such as diapers, can provide ordinary combinations of intake, distribution, and retention functions. There has, however, been a continued need for improved materials and improved systems and structures which provide improved combinations having increased levels of the intake, distribution and retention functions. To provide improved leakage resistance, the present invention incorporates improved materials, where the materials exhibit improved properties in at least one of the functional areas. As a result, the overall performance of the system can be improved.

The intake function can, for example, be adjusted by controlling factors such as the fiber and particle sizes of the materials in the relevant layer region, the layer-region porosity, the layer-region basis weight, and the layer-region composition. The distributing or distribution function can, for example, be adjusted by controlling factors such as the fiber and particle sizes of the component materials, the liquid contact angles provided for by the materials, the liquid surface tensions provided by the liquid, and the basis weights of the materials.

To further improve the desired balance of absorbent properties, there have been identified a number of important factors which can allow the layer regions to better work in combination, and thereby provide an improved overall system performance. The factors include a desired Flow Conductance Value and a desired Liquid Wicking Value provided by the absorbent system. An additional factor is a combined Conductance-Wicking value provided by the system.

The Flow Conductance is a value which is based on the physical properties of the absorbent materials, particularly the absorbent materials which are disposed in the target area of the absorbent system, and is related to the intake capability provided by the absorbent core structure. Desirably, the Flow Conductance Value has a minimum of not less than about $2.5*10^{-6}$ cm$^3$. Alternatively, the Flow Conductance Value is not less than $3*10^{-6}$ cm$^3$, and optionally, is not less about $3.5*10^{-6}$ cm$^3$ to provide improved performance. In further aspects of the invention, the Flow Conductance Value can be up to about $5*10^{-6}$ cm$^3$. Alternatively, the Flow Conductance Value can be up to about $7*10^{-6}$ cm$^3$, and optionally, can be up to about $9*10^{-6}$ cm$^3$, or greater to provide improved performance.

The Liquid Wicking Potential Value (Liquid Wicking Value) is a performance parameter which pertains to the amount of liquid removed from a described target area of the absorbent structure during a vertical wicking operation. This value represents the ability of the absorbent structure to remove fluid from the target area between insults, and at least one layer region of the absorbent system is configured to provide the desired Liquid Wicking Potential Value. Desirably, at least one layer of the absorbent system, particularly at least one primary layer region of the absorbent core, can provide a Liquid Wicking Value of not less than a minimum of about 10%. Alternatively, the provided Liquid Wicking Value is not less than about 15% and optionally, is not less than about 20%. In further aspects of the invention, the absorbent system can provide a Liquid Wicking Value of up to about 60%. Alternatively, the provided Liquid Wicking Value can be up to about 65%, and optionally, can be up to about 70% or greater to provide further improved performance.

The Combined Conductance-Wicking value (C) of the system can be at least about $14*10^{-6}$ cm$^3$. Alternatively, the Combined Conductance-Wicking value can be at least about $17*10^{-6}$ cm$^3$, and optionally can be at least about $20*10^{-6}$ cm$^3$ to provide an improved balance of performance. In other desired arrangements, the Combined Conductance-Wicking value can be at least about $15*10^{-6}$ cm$^3$, alternatively can be at least about $16*10^{-6}$ cm$^3$, and optionally can be at least about $18*10^{-6}$ cm$^3$ to provide further desired benefits.

In thin absorbent designs with narrow crotch sections, the target area of the product, in its dry state, ordinarily does not have enough void volume available to efficiently absorb the initial insult of liquid, such as urine. This lack of void volume can be compensated for by incorporating a particularly configured SAP in an amount sufficient to absorb the incoming liquid during the time of the insult. The incorporated SAP is configured to acquire and hold the amount of fluid which is to be absorbed during the insult to provide the desired leakage resistance.

Although some of these parameters have individually been discussed in the past, it is has remained difficult to provide an effective combination of these attributes within a single composite structure, while maintaining desirable consumer attributes. The difficulties faced in the past have typically involved a desire to have a relatively low SAP content, either in the entire structure or within an individual layer, to enhance wicking capability. Where the low SAP concentration is used throughout the product, an excessively large product thickness may be needed to provide the desired absorbent capacity. Attempts have been made to provide one absorbent layer with a low SAP concentration to promote wicking, while maintaining high SAP concentrations in another other layer to achieve a thin product having the desired amount of absorbent capacity. Such systems have not provided the desired levels of performance because the liquid can preferentially move into the areas containing relatively higher concentrations of SAP. In the layer region containing the relatively low concentration of SAP, the amount of remaining liquid can be insufficient to provide the desired levels of wicking.

To overcome these shortcomings, a particular aspect of the invention can include a controlled-rate SAP in the absorbent system. Through the use of a controlled-rate SAP, such as a selected, attenuated rate SAP, the concentration of liquid in a fibrous structure of appointed distributing layer region can be kept high even when the distributing layer region contains selected amounts of SAP. In particular arrangements, the controlled slow-rate SAP is primarily located in a layer region which is other than the distributing layer. As a result, the low SAP layer can selectively become saturated, while the overall absorbent capacity within a thin product design is maintained at a desired high level. It is contemplated that alternative mechanisms, other than the incorporation of the slow rate SAP, may be used to provide the desired apportioning and differences in the concentrations of the absorbed liquid between the selected layer regions. For example, the desired apportioning may be generated by selectively configuring the relative wettability and/or density of the layer regions.

Figure 2:
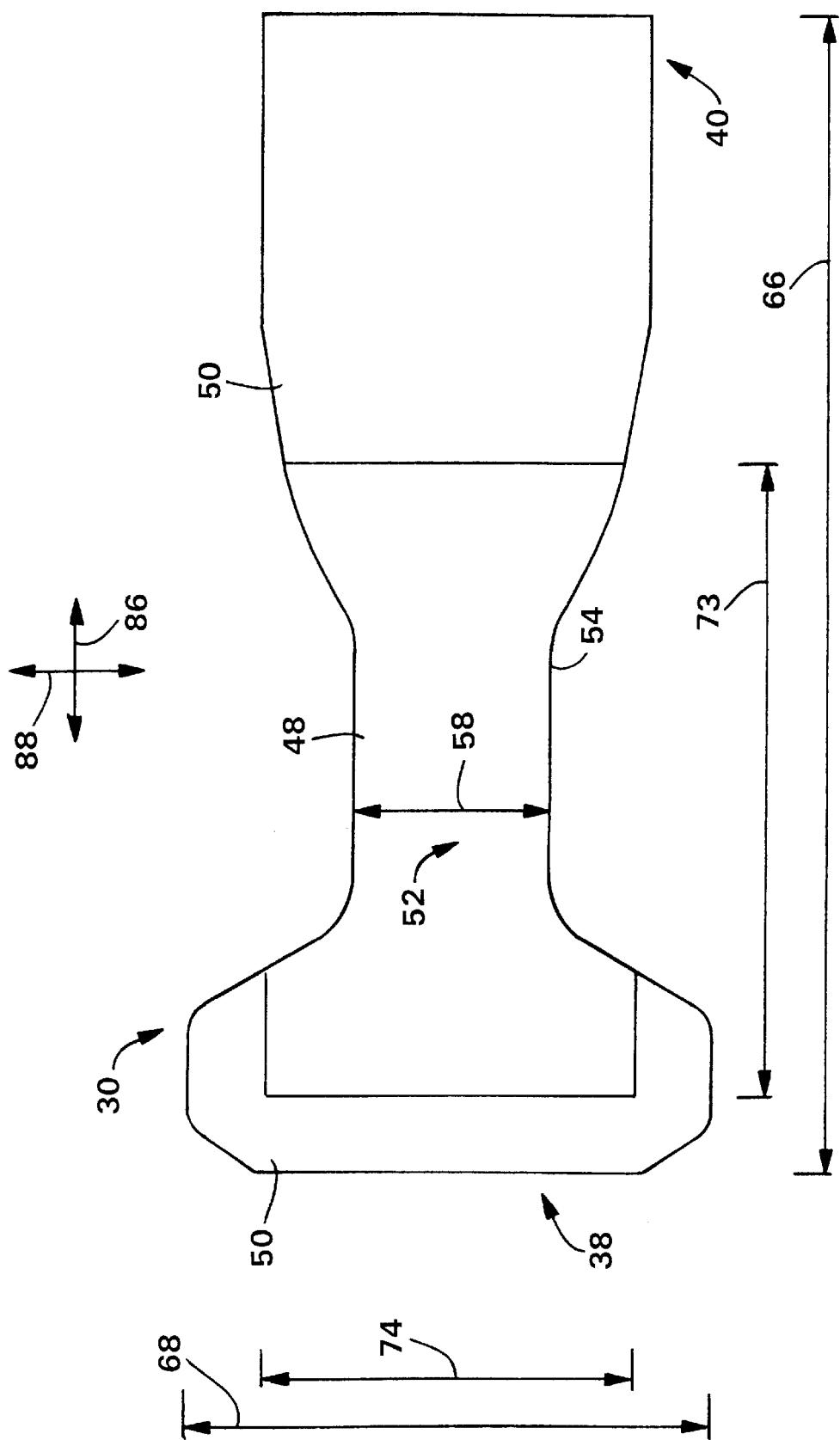
FIG. 2 representatively shows a top view of the structure of an absorbent core of the invention having a first, top layer region which extends over a medial portion of the total area of the absorbent core, and a second, bottom layer region which extends over substantially the entire area of the absorbent core, where the opposed, longitudinal end edges of the first layer region are spaced from each of the opposed, longitudinal end edges of the second layer region.

With reference to FIGS. 1 and 2, an absorbent composite system 26 of the invention includes a surge management portion 84, and an absorbent pad or core structure 30. The absorbent core 30 has multiple absorbent layer regions, and the properties of the individual layer regions are selected and arranged to provide improved leakage performance by balancing the intake and wicking properties of the absorbent components.

Generally stated, the absorbent core 30 of the present description, begins at the first layer which includes superabsorbent (as determined when moving from the innermost, bodyside surface of the article towards the outermost surface of the article), along with any immediate component needed to maintain the integrity of such layer during functional testing. Such first layer desirably includes a minimum of not less than about 5 wt % superabsorbent. The absorbent core ends at the last absorptive layer which is positioned immediately prior to the substantially liquid-impermeable layer which is appointed for preventing leakage from the diaper, as determined when moving from the innermost, bodyside surface of the article towards the outermost surface of the article. Accordingly, the absorbent core 30 of the shown configurations includes the first primary absorbent layer 48, the outermost layer of wrapsheet 28, and the components sandwiched therebetween. The absorbent core of the illustrated configuration excludes the topsheet layer 24, the surge management layer 84 which does not contain superabsorbent, and the backsheet layer 22.

The appropriate balance of intake and wicking properties can be represented by various determining factors, such as the Flow Conductance Value, Wicking Potential Value, basis weight, density, particle size, fiber size, relative amount of fiber, and the like, as well as combinations thereof. The Flow Conductance Value of the absorbent relates to the available void volume and permeability of the structure throughout the various saturation levels typically encountered during ordinary use. To provide improved performance for the absorbent system, the liquid should be allowed to enter the absorbent structure at a rate which is as near as possible to the rate at which the liquid is delivered onto the absorbent composite structure. The Flow Conductance Value can help characterize the intake potential of the overall, absorbent system 26, and can particularly help characterize the intake potential of the absorbent core 30. In addition, it is important to move the liquid away from the entry area for storage in more remote areas of the absorbent system to thereby recondition and prepare the entry area to more efficiently receive the next insult of liquid. The Liquid Wicking Value can help characterize the ability of the absorbent structure to remove fluid from the target area between insults.

Figure 2A:
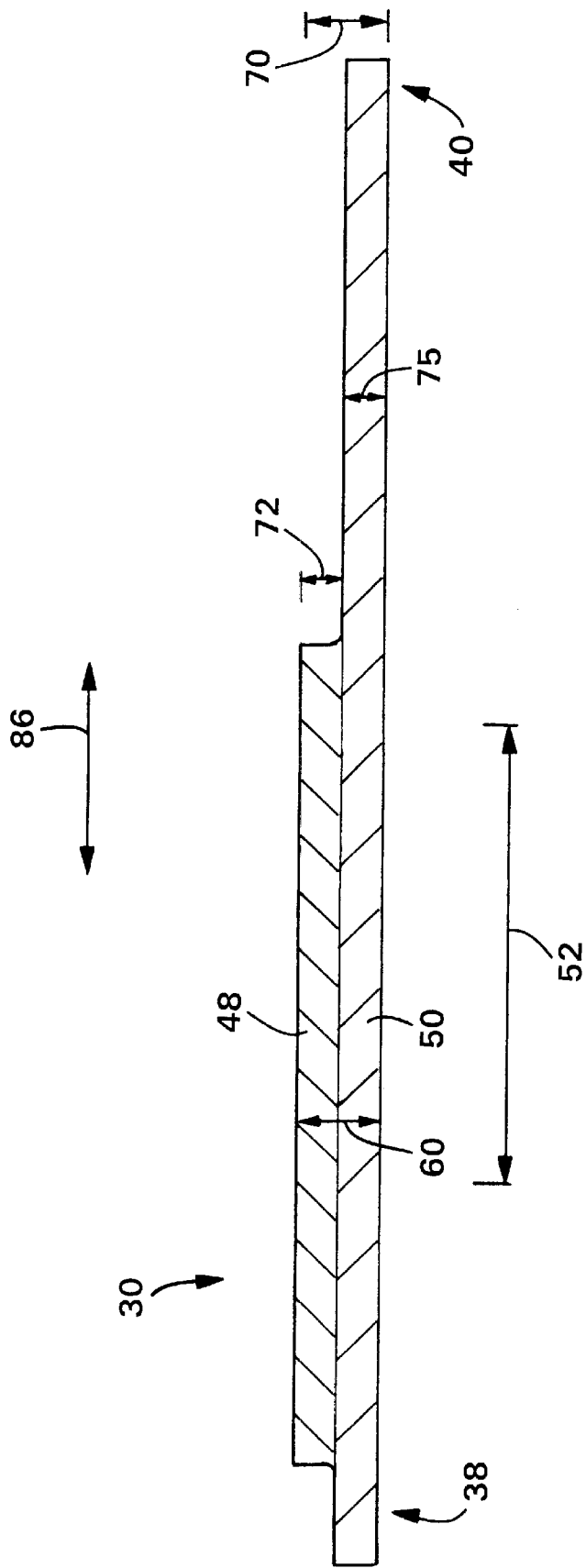
FIG. 2A representatively shows a longitudinal cross-sectional view of the absorbent core of FIG. 2.

With reference to FIGS. 2 and 2A, the absorbent core 30 has an overall composite core length 66, an overall composite core width 68, an overall composite core thickness 70, a crotch core width 58 and an appointed front-most edge. The front-most edge is appointed for placement in a front waistband section of the article. The overall composite assembly of the absorbent core 30 extends over and covers an overall core area, as illustrated in FIG. 2. The individual core component layers and optional sublayers may extend over the entire absorbent core area, or may extend over a selected portion of the core area, as desired to provide desired performance. In addition, each of the individual layer regions has individual dimensions. In the representatively shown arrangement, for example, a first layer region 48 has a first thickness or height 72, a first length 73 and a first width 74. A second layer region has a second thickness or height 75, a second length 66 and a second width 68.

With respect to the overall length 66 of the absorbent core 30, the intended intake, target area 52 of the absorbent structure is a region of the absorbent core which begins at a laterally extending, cross-directional line located 24% of the length of the absorbent composite core length 66 away from a terminal, front-most edge of the absorbent core, and extends to a cross-directional line located 59% of the absorbent composite length away from the front-most edge of the absorbent core. In the illustrated arrangement, for example, the target area of the absorbent core can be an area of the absorbent structure which begins at a laterally extending line located approximately 3.5 inches (89 mm) from the terminal, front-most edge of the absorbent core and extends to a laterally extending line located approximately 8.5 inches (216 mm) from the front-most edge of the absorbent core.

It has been undesirable to increase the Flow Conductance Value by increasing the bulk of the absorbent core structure, because the product thickness can become excessive in articles having a narrow crotch width. As a result, there has been a continuing need for configurations which can provide the desired intake performance, such as represented by the Flow Conductance Value, while maintaining a thin absorbent core 30 and a thin absorbent system 26. Desirably, the total thickness of the dry absorbent core 30 is not more than about 6 mm. Alternatively, the thickness of the absorbent core can be not more than about 5.3 mm, and optionally, the thickness of the absorbent core can be not more than about 5 mm to provide desired benefits. In another aspect of the invention, the thickness of the dry absorbent core 30 can be not more than about 25% of the crotch width of the absorbent core. Alternatively, the dry absorbent core thickness can be not more than about 20% of the crotch width of the absorbent core, and optionally, can be not more than about 15% of the crotch width of the absorbent core to provide improved benefits. For the purposes of the present disclosure, the crotch width of the absorbent core is determined at a narrowest (smallest) lateral dimension of the crotch region located within the target area 52 of the core.

Desirably, the overall total thickness of the dry absorbent system 26 is not more than about 8 mm. Alternatively, the thickness of the absorbent system can be not more than about 7.3 mm, and optionally, the thickness of the absorbent system can be not more than about 7 mm to provide desired benefits. In another aspect of the invention, the overall thickness of the dry absorbent system 26 can be not more than about 30% of the crotch width of the absorbent system. Alternatively, the dry absorbent core thickness can be not more than about 25% of the crotch width of the absorbent system, and optionally, can be not more than about 20% of the crotch width of the absorbent system to provide improved benefits.

For the purposes of the present disclosure, the dry thickness is measured at a restraining pressure of 0.2 psi (1.38 KPa).

In a further aspect of the invention, the low bulk absorbent system 26, and particularly the absorbent core 30, can have a crotch region 54 appointed for placement between a wearer's legs wherein a narrowest (smallest) lateral dimension of the crotch region located within the target area 52 provides a minimum crotch width 58. Accordingly, an adult product (intended for use by a person over the age of 13 years), can have a crotch width the minimum lateral dimension of which is not more than about 5.5 inches (about 14 cm) when the absorbent composite is dry. Alternatively, the minimum crotch width 58 can be not more than about 4.5 inches (about 11.4 cm), and optionally can be not more than about 3.5 inches (about 8.9 cm) to provide improved fit and comfort. A non-adult product (intended for use by a person of age 13 years or less), can have a crotch width the minimum lateral dimension which is not more than about 4 inches (about 10 cm) when the absorbent composite is dry. Alternatively, the minimum crotch width 58 can be not more than about 3 inches (7.6 cm), and optionally can be not more than about 2 inches (5.1 cm) to provide improved fit and comfort for the non-adult persons.

It is also important to remove liquid from the target area 52 of the absorbent system to effectively avoid an over-saturation of this area and leakage from the article. The ability of the absorbent system to move liquid away from the target region can be represented by the Liquid Wicking Value provided by the system. The Wicking Potential Value is related to the amount of liquid which the system is capable of moving out of the target area when the target area has a liquid loading/saturation level of 1.0 gram of liquid per square centimeter of the target area of the absorbent composite. Therefore, the present invention provides a distinctively layered absorbent system which is thin, is narrow in the crotch region and exhibits low bulk.

The layer regions in the absorbent system are arranged to include a bodyside first layer region which can be of various suitable configurations, but typically has a size which is no larger than the size of the outermost, second absorbent layer region. This first, upper layer region can maintain a low saturation level throughout the use of the absorbent article, and can maintaining a high Flow Conductance Value when used in combination with the, second, lower layer region. The lower layer region can be selectively shaped, such as with an hourglass or "T" configuration, and is configured to efficiently distribute and move liquid out from the target area of the absorbent composite. In particular, the second, lower layer region is capable of providing the desired values of Liquid Wicking Potential, as can be determined by the Liquid Wicking Potential Value procedure described hereinbelow.

Figure 1A:
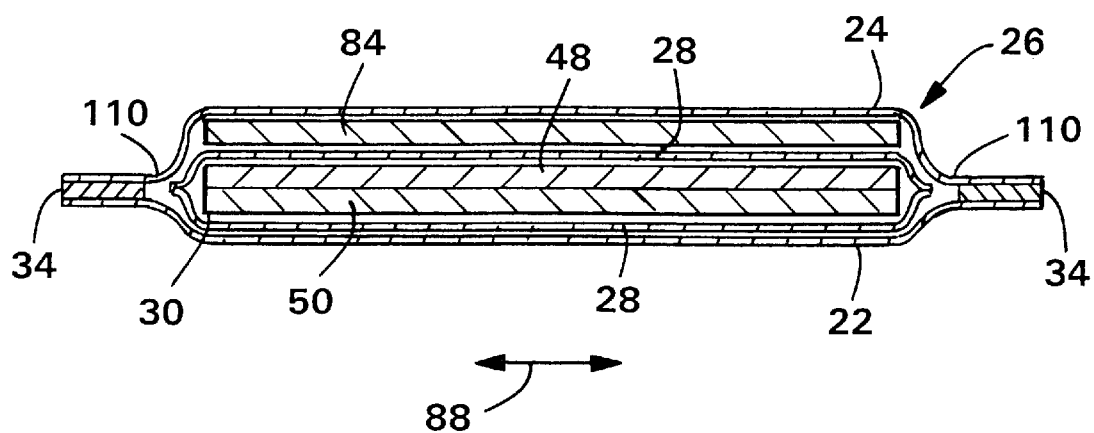
Figure 1B:
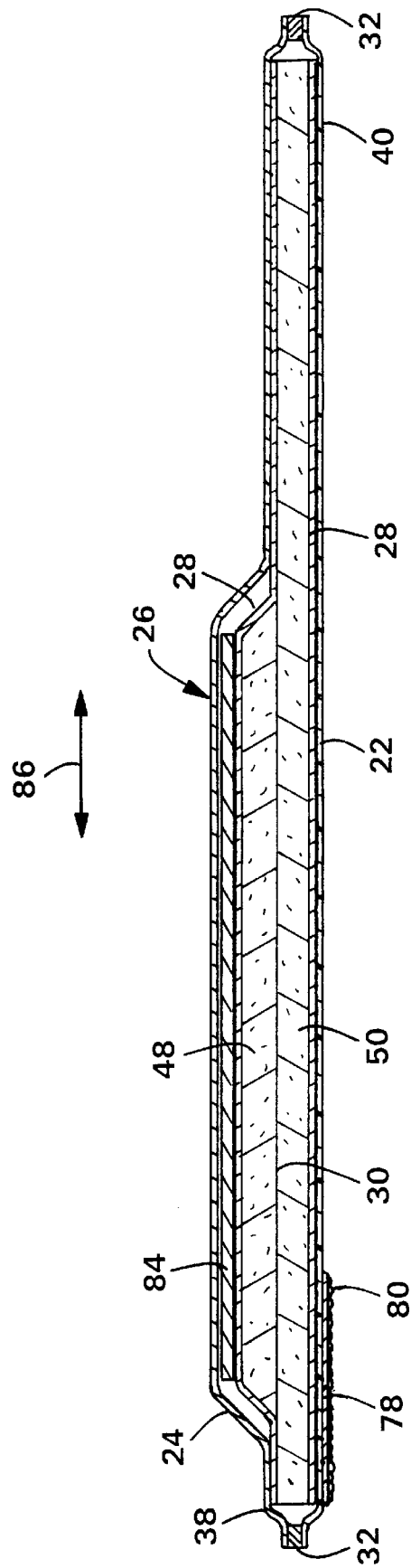

With reference to FIGS. 1, 1A and 1B, the invention can provide an absorbent garment article, such as a diaper 20, having a longitudinal, length-wise direction 86, and a lateral, cross-wise direction 88. The article has a first waistband section, such as rear waistband section 40, a second waistband section, such as front waistband section 38, and an intermediate section 42 which interconnects the first and second waistband sections. The front waistband section 38 has a laterally opposed, front pair of side edge regions 118, the rear waistband section 40 has a laterally opposed, rear pair of side edge regions, 116, and the intermediate section 42 provides an article crotch region for placement between a wearer's legs.

FIG. 1 is a representative plan view of the representative disposable diaper 20 of the present invention in its flat-out, uncontracted state (i.e., with substantially all elastic induced gathering and contraction removed). Portions of the structure are partially cut away to more clearly show the interior construction of the diaper article, and the bodyside surface of the diaper which contacts the wearer is facing the viewer. The outer edges of the diaper define a periphery with longitudinally extending side edge margins 110 and laterally extending end edge margins 112. The side edges define leg openings for the diaper, and optionally, are curvilinear and contoured. The end edges are shown as straight, but optionally, may be curvilinear.

A liquid permeable topsheet layer 24 is superposed in facing relation with a backsheet layer 22, and the absorbent system is operably connected and affixed between the backsheet layer 22 and topsheet layer 24. The representatively shown configuration has an absorbent composite system 26 which includes a surge management portion 84 and a retention portion for holding and storing liquid. The retention portion of the illustrated absorbent system includes the absorbent core 30. In the shown configuration, the surge management portion 84 is a layer positioned between the absorbent core 30 and the topsheet layer 24. Other arrangements may also be employed. For example, the surge layer 84 may optionally be positioned between the absorbent core and the backsheet layer 22, or on the bodyside surface of the topsheet.

The article typically includes elastomeric members, such as leg elastics 34 and waist elastics 32, and the surge management portion is positioned in an operative liquid communication with the retention portion of the absorbent article. The topsheet 24, backsheet 22, absorbent core 30, surge management portion 84 and elastic members 34 and 32 may be assembled together into a variety of well-known diaper configurations. The diaper can additionally include a system of containment flaps 82, and side panel members 90 which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993. Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995; in U.S. patent application Ser. No.

286,086 of D. Fries, entitled A PROCESS FOR ASSEMBLING ELASTICIZED EAR PORTIONS and filed Aug. 3, 1994 which issued as U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 which issued as U.S. Pat. No. 5,595,618. The disclosures of the above-described documents are incorporated herein by reference in a manner that is consistent (not in conflict) herewith.

Diaper 20 generally defines the longitudinally extending length direction 86 and the laterally extending width direction 88, as representatively shown in FIG. 1. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 24 and backsheet 22 may be generally coextensive, and may have length and width dimensions which are generally larger than and extend beyond the corresponding dimensions of the absorbent structure 26 to provide for the corresponding side margins 110 and end margins 112 which extend past the terminal edges of the absorbent structure. The topsheet 24 is associated with and superimposed on the backsheet 22, thereby defining the periphery of the diaper 20. The waistband regions comprise those portions of the diaper, which when worn, wholly or partially cover or encircle the waist or mid-lower torso of the wearer. The intermediate, crotch region 42 lies between and interconnects the waistband regions 38 and 40, and comprises that portion of the diaper which, when worm, is positioned between the legs of the wearer and covers the lower torso of the wearer. Thus, the intermediate crotch region 42 is an area where repeated surges of liquid typically occur in the diaper or other disposable absorbent article.

The backsheet 22 can typically be located along an outer-side surface of the absorbent composite 26 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. Backsheet 22 prevents the exudates contained in absorbent composite 26 from wetting articles, such as bedsheets and overgarments, which contact diaper 20. In particular embodiments of the invention, backsheet 22 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or non-woven fibrous web layer which has been totally or partially constructed or treated to impart the desired levels of liquid impermeability to selected regions that are adjacent or proximate the absorbent composite. For example, the backsheet may include a gas-permeable, non-woven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene blown film and a 0.7 ounce per square yard (23.8 gsm) polypropylene spunbond material (2 denier fibers). A material of this type forms the outercover of a HUGGIES SUPREME diaper, which is commercially available from Kimberly-Clark Corporation. The backsheet 22 typically provides the outer cover of the article. Optionally, however, the article may include a separate outer cover component member which is additional to the backsheet.

Backsheet 22 may alternatively include a micro-porous, "breathable" material which permits gases, such as water vapor, to escape from absorbent composite 26 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component such as the backsheet 22 or the containment flaps 82 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31, 1968, or a substantially equivalent procedure.

The size of the backsheet 22 is typically determined by the size of absorbent composite 26 and the particular diaper design selected. Backsheet 22, for example, may have a generally T-shape, a generally I-shape or a modified hourglass shape, and may extend beyond the terminal edges of absorbent composite 26 by a selected distance, such as a distance within the range of about 1.3 centimeters to 2.5 centimeters (about 0.5 to 1.0 inch), to provide at least a portion of the side and end margins.

Topsheet 24 presents a body-facing surface which is compliant, soft-feeling, and non-irritating to the wearer's skin. Further, the topsheet 24 can be less hydrophilic than absorbent composite 26, and is sufficiently porous to be liquid permeable, permitting liquid to readily penetrate through its thickness to reach the absorbent body composite. A suitable topsheet layer 24 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 24 is typically employed to help isolate the wearer's skin from liquids held in absorbent composite 26.

Various woven and nonwoven fabrics can be used for topsheet 24. For example, the topsheet may be composed of a meltblown or spunbonded web of the desired fibers, and may also be a bonded-carded-web, hydroentangled web, needled web or the like, as well as combinations thereof. The various fabrics can be composed of natural fibers, synthetic fibers or combinations thereof. Optionally, the topsheet may include a net material or an apertured film.

For the purposes of the present description, the term "nonwoven web" means a web of fibrous material which is formed without the aid of a textile weaving or knitting process. The term "fabrics" is used to refer to all of the woven, knitted and nonwoven fibrous webs, as well as combinations thereof.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 24 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant. The surfactant can be applied by any conventional means, such as spraying, printing, brush coating or the like.

The topsheet 24 and backsheet 22 are connected or otherwise associated together in an operable manner. As used herein, the term "associated" encompasses configurations in which topsheet 24 is directly joined to backsheet 22 by affixing topsheet 24 directly to backsheet 22, and configurations wherein topsheet 24 is indirectly joined to backsheet 22 by affixing topsheet 24 to intermediate members which in turn are affixed to backsheet 22. Topsheet 24 and backsheet 22 can, for example, be affixed directly to each other in the diaper periphery by attachment means (not shown) such as adhesive bonds, sonic bonds, thermal bonds, pinning, stitching or any other attachment means known in the art, as well as combinations thereof. For example, a uniform continuous layer of adhesive, a patterned layer of adhesive, a sprayed pattern of adhesive or an array of separate lines, swirls or spots of construction adhesive may be used to affix topsheet 24 to backsheet 22. It should be readily appreciated that the above-described attachment means may also be employed to suitably interconnect, assemble and/or affix together the various other component parts of the articles which are described herein.

The representatively shown article has an absorbent system which includes the surge layer 84 and the retention portion for holding and storing absorbed liquids and other waste materials. In particular aspects of the invention, the retention or storage portion is provided by the shown absorbent core structure 26 which is composed of multiple layers of selected fibers and high-absorbency particles. The shown configuration of the absorbent composite is positioned and sandwiched between topsheet 24 and backsheet 22 to form the diaper 20. The absorbent composite has a construction which is generally compressible, conformable, non-irritating to the wearer's skin, and capable of absorbing and retaining body exudates.

In the various configurations of the invention, many suitable types of wettable, hydrophilic fibrous material can be used to form any of the various component parts of the absorbent article. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used in the present description, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles equal to or greater than 90° are designated "nonwettable".

In particular, the absorbent core structure 30 can comprise one or more matrices of fibers, such as a web of natural fibers, synthetic fibers and the like, as well as combinations thereof. Desirably the fibers are hydrophilic, either naturally or through the effects of a conventional hydrophilic treatment. Particular arrangements can include a fibrous matrix composed of cellulosic woodpulp fluff. It should be readily appreciated that each of the primary layer regions 48 and 50 can include the same types of fibrous matrices or may include different types of fibrous matrices.

In particular aspects of the invention, the fibers in one or more of the primary layers 48 and 50 can be mixed or otherwise incorporated with particles of high-absorbency material. The fibers in the selected layer or layers are arranged in an absorbent matrix, and desirably, each of the layers 48 and 50 can include fibers combined with particles of the high-absorbency material. In particular arrangements, for example, the appointed layer of the absorbent core 30 may comprise a mixture of superabsorbent hydrogel-forming particles and natural fibers, synthetic polymer melt-blown fibers, a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of each layer of the absorbent structure, with lower concentrations toward the bodyside of the absorbent composite and relatively higher concentrations toward the outside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of each layer of the absorbent structure, with higher concentrations toward the bodyside of the absorbent composite and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent composite include natural and modified natural polymers, such as hydrolyzed acrylonitrilegrafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the absorbent core 30 can be a superabsorbent gelling material, and the superabsorbent can be generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Optionally, conglomerates of particles of absorbent gelling material may also be used in absorbent composite 26. Desired for use are particles having an average size of from about 5 microns to about 1 millimeter. "Particle size" as used herein means the weighted average of the smallest dimension of the individual particles.

In particular aspects of the invention, the absorbent gelling material particles can have a Modified Absorbency Under Load (MAUL) of at least about 20 grams of absorbed liquid per gram of absorbent material (g/g). Desirably, the superabsorbent material can have a MAUL of at least about 24 g/g, and more desirably can have a MAUL of at least about 27 g/g. In further aspects, the absorbent material can exhibit a MAUL of up to about 30 g/g or more. The MAUL value can be measured using the MAUL test method described in the Testing Procedures section of the present description.

The hydrophilic fibers and high-absorbency particles in the total composite core 30 can be configured to form an average composite basis weight which is within the range of about 400–900 gsm (g/m$^2$). In certain aspects of the invention, the average composite basis weight is within the range of about 500–800 gsm, and preferably is within the range of about 550–750 gsm to provide desired performance.

In particular aspects of the invention, the high-absorbency material can include a superabsorbent nonwoven material. The superabsorbent nonwoven is a nonwoven material which is composed of superabsorbent fibers alone or is composed of a composite of superabsorbent fibers and other materials. The superabsorbent nonwoven material has a high ultimate liquid storage capacity when immersed in a liquid, particularly a 0.9% saline solution, with a liquid holding capacity of at least about 10 grams of absorbed liquid per gram of absorbent material (g/g). Alternatively, the liquid holding capacity is at least about 20 g/g, and optionally is at least about 30 g/g to provide improved performance characteristics. The superabsorbent nonwoven is selectively configured to promote liquid intake, liquid storage, liquid distribution, or some combination of these functions. In particular, the superabsorbent nonwoven can be engineered to perform a specific function or set of functions when the superabsorbent nonwoven is incorporated as a layer or component in a product having a multilayered absorbent structure.

To limit any undesired movement of the high-absorbency material, the article can include an absorbent composite 26 having an over-wrap, such as wrap sheet 28, which is placed immediately adjacent and around the entire absorbent core 30, around an individual layer region of the core, or around one or more selected components of the absorbent composite, as desired. In addition, the wrap sheet may be bonded to the absorbent composite structure and to the various other components of the article. The wrap sheet is preferably a layer of absorbent material which covers the major bodyside and outerside surfaces of the absorbent composite, and preferably encloses substantially all of the peripheral edges of the absorbent composite to form a substantially complete envelope thereabout. Alternatively, the wrap sheet can provide an absorbent wrapping which covers the major bodyside and outerside surfaces of the absorbent composite, and encloses substantially only the lateral side edges of the absorbent composite. Accordingly, both the linear and the inwardly curved portions of the lateral side edges of the wrap sheet would be closed about the absorbent composite. In such an arrangement, however, the end edges of the wrap sheet may not be completely closed around the end edges of the absorbent composite at the waistband regions of the article.

For example, the complete wrap sheet 28, or at least the bodyside layer of the wrap sheet, may comprise a meltblown web composed of meltblown fibers, such as meltblown polypropylene fibers. Another example of absorbent wrap 28 may comprise a low porosity cellulosic web, such as a tissue composed of an approximately 50/50 blend of hardwood/softwood fibers.

The absorbent wrap 28 may comprise a multi-element wrapsheet which includes a separate bodyside wrap layer and a separate outerside wrap layer, each of which extends past all or some of the peripheral edges of the absorbent core 30. Such a configuration of the wrap sheet can, for example, facilitate the formation of a substantially complete sealing and closure around the peripheral edges of the absorbent core 30. In the back waistband portion of the illustrated diaper, the absorbent wrap may also be configured to extend an increased distance away from the periphery of the absorbent core to add opacity and strength to the back sidesections of the diaper. In the illustrated embodiment, the bodyside and outerside layers of absorbent wrap 28 can extend at least about ½ inch beyond the peripheral edges of the absorbent core to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 28 may be composed of substantially the same material, or may be composed of different materials. For example, the outside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outside layer can help reduce costs.

Figure 7:
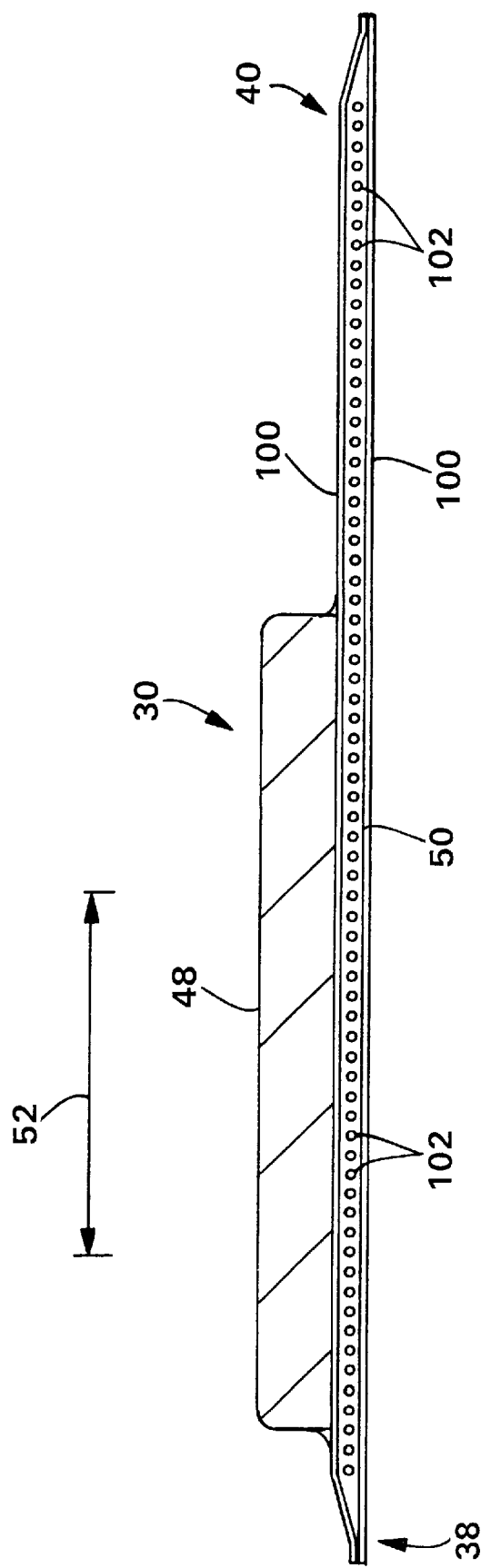
FIG. 7 representatively shows a longitudinal, cross-sectional view of an absorbent core of the invention which includes a bottom layer region composed of a laminate having superabsorbent particles sandwiched and held between layer regions of liquid permeable material.
Figure 8:
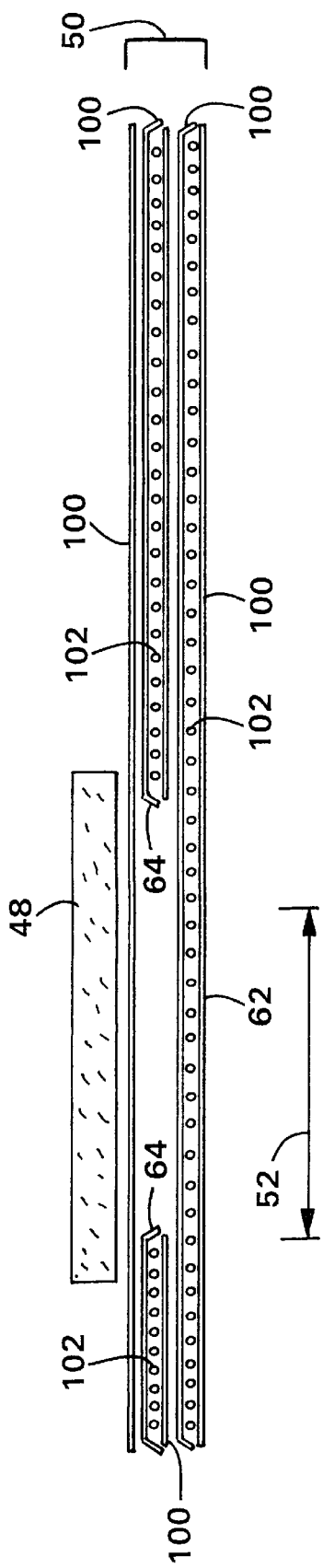
FIG. 8 representatively shows a longitudinal, cross-sectional view of another absorbent core of the invention which includes a second, bottom layer region composed of a plurality of heterogeneous, sublayer laminates arranged to provide a nonuniform, zoned basis weight within the bottom layer region.
Figure 9:
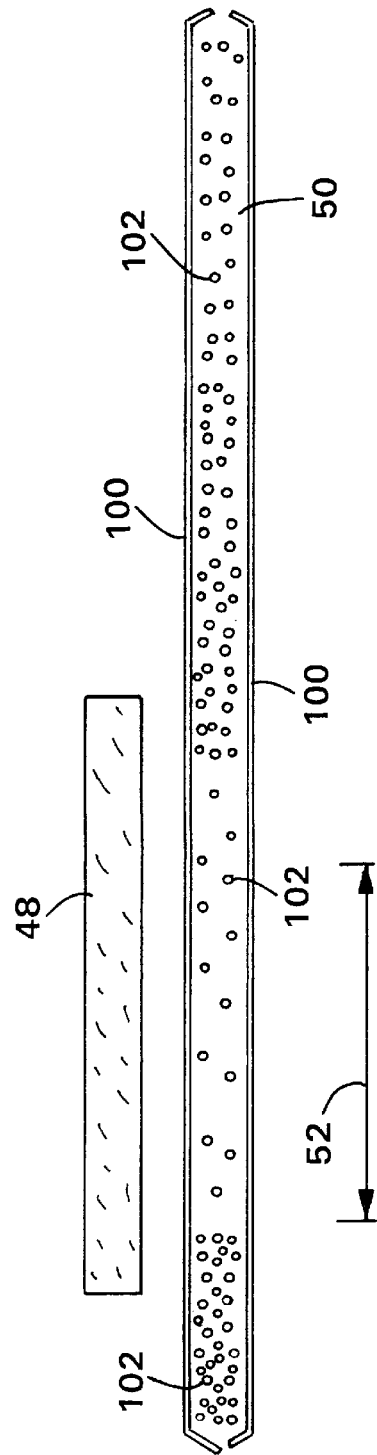
FIG. 9 representatively shows a longitudinal, cross-sectional view of another absorbent core of the invention which includes a bottom layer region composed of a heterogeneous laminate wherein the distribution of superabsorbent material is arranged to provide a nonuniform, zoned basis weight of superabsorbent within the bottom layer region.

With reference to FIGS. 7, 8 and 9, another absorbent core of the invention can include a component having particles of superabsorbent material 102 operatively held between layers of liquid permeable material 100, such as layers of tissue, open cell foam, porous films, woven fabric, nonwoven fabric or the like, as well as combinations thereof. In particular aspects of the invention, the bottom layer 50 may be composed of a laminate having superabsorbent particles sandwiched or otherwise held between layers of carrier tissue held with water-sensitive attachments. Examples of such configurations are described in U.S. Pat. No. 5,593,399 issued Jan. 14, 1997 to R. Tanzer et al. and entitled ABSORBENT ARTICLE WHICH INCLUDES SUPERABSORBENT MATERIAL LOCATED IN DISCRETE, ELONGATE POCKETS PLACED IN SELECTED PATTERNS, the entire disclosure of which is incorporated by reference in a manner that is consistent herewith.

With reference again to FIGS. 1 and 2, the diaper 20 can also include a surge management layer 84 which helps to decelerate and diffuse surges of liquid that may be directed into the retention and storage portion of the absorbent article. The surge layer 84 can, for example, be located on an inwardly facing body side surface of topsheet layer 24. In the representatively shown configuration, surge layer 84 is located adjacent to an outer side surface of the topsheet layer. Accordingly, the surge layer is interposed between the topsheet 24 and absorbent core 30. Examples of suitable surge management layers 84 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 which issued as U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 which issued as U.S. Pat. No. 5,490,846; the entire disclosures of which are hereby incorporated by reference in a manner that is consistent herewith.

With reference to FIGS. 1 and 2, particular aspects of the invention can include an absorbent composite which includes a selected plurality of two or more primary, layer-region components. The configuration of the illustrated multilayer absorbent core 30, for example, includes a first layer-region 48 and at least a second layer-region 50.

The representatively shown first layer region 48 provides a relatively upper layer region which is positioned on the bodyside region of the absorbent core 30 and is relatively more closely adjacent to the topsheet layer 24. The illustrated second layer region 50 provides a relatively lower layer region which is positioned on the outward-side region of the absorbent core and is relatively more closely adjacent to the backsheet layer 22.

In a desired aspect of the invention, the components in the various layer regions, such as the layer regions 48 and/or 50, can include a blend or other matrix of high bulk fibers. High bulk fibers are those which impart improved bulk retention and/or recovery from deformation. The high bulk fibers can particularly provide wet bulk retention, and/or wet recovery from deformation when the fibers are incorporated into materials which become wetted. Examples of suitable high bulk fibers include synthetic, thermoplastic fibers, synthetic fibers composed of natural polymers such as cellulose, and natural fibers, as well as combinations thereof. The resiliency of fibers composed of natural polymers can be enhanced by chemical crosslinking and/or by imparting kink and/or curl to the fiber.

The high bulk fibrous materials are able to exhibit a lower density in both their wet state and dry state, and thereby increase the permeability and thickness, thus increasing the Flow Conductance Value. For example, high bulk wood pulp fibers can be achieved through various techniques, such as through chemical and/or mechanical modifications of the pulp fibers. Examples of suitable high bulk fibers include mercerized fibers, crosslinked cellulose fluff pulp fibers and the like, as well as combinations thereof.

In another aspect of the invention, the components in the various layer regions, such as the layer regions 48 and/or 50, can be composed of a blend or other matrix of the high bulk fibers, and a controlled-rate superabsorbent. The controlled-rate superabsorbent is a material, such as a superabsorbent polymer material, which demonstrates a modified absorbency-under-load (MAUL) value of at least a minimum of about 20 g/g.

In a further aspect of the invention, the desired controlled-rate superabsorbent can exhibit a particular absorbency rate, Tau ($\tau$) value, such as a Tau value which is at least a minimum value of about 0.4 min. Desirably, the superabsorbent Tau value is at least about 1 min, and can be at least about 2 min to provide improved performance. In still other aspects the Tau value can be up to about 40 minutes or more. In other aspects, the absorbent core, particularly the different layer regions of the absorbent core, can advantageously incorporate a selected combination of superabsorbent materials wherein at least a selected pair of different superabsorbent materials are configured to provide a Tau-value-ratio which is equal to or greater than about 2:1. The Tau-value-ratio can optionally be up to about 5:1, or more, to provide further benefits. Desirably, the superabsorbent material having the relatively greater Tau value is positioned relatively closer to the bodyside surface of the absorbent core. A suitable technique for determining the Tau value of each superabsorbent is described in the Flooded Absorbency Under Zero Load procedure set forth in the present description.

A particular controlled-rate superabsorbent can be a superabsorbent wherein the individual superabsorbent particles are treated with a hydrophobic coating to provide a selected delay in the absorption of aqueous liquids into the particles. For example, the superabsorbent may be a coated particulate superabsorbent. The particles have absorbent centers composed of a partial sodium salt of a cross-linked polyproponic acid (prepared by the process described in U.S. Pat. No. 5,629,377), and the particle centers are covered with a hydrophobic silicone elastomer coating. A representative controlled-rate superabsorbent of this type is available from DOW Chemical Company, a business having offices in Midland, Mich, U.S.A.

An alternative controlled-rate superabsorbent can be configured with relatively large particle sizes to provide particles having a low, surface area to volume ratio which thereby produces the desired absorbency rate. The controlled-rate superabsorbent particles can also have a substantially spherical or other three-dimensional shape which operatively generates the desired low ratio of surface-area-to-volume and delayed absorbency rate.

In addition, the bulk chemistry of the superabsorbent polymer can be modified to provide the desired, delayed absorbency rate. For example, the controlled-rate superabsorbent may incorporate an anionic polyelectrolyte which is reversibly crosslinked with a polyvalent metal cation. A water soluble complexing agent may be configured to reverse the crosslinking.

Alternative controlled-rate superabsorbents can be encased by a coating or other treatment which operatively slows the diffusion of liquid into the superabsorbent particles, or repels liquid in a manner which provides the desired delayed absorbency rate. The coatings or treatments may be elastic or inelastic, and the coating or treatment may be hydrophobic or hydrophilic. The coatings may erode, dissolve, or crack in a controlled fashion to provide the desired absorbency characteristics. Optionally, the absorbency rate may be limited and/or controlled by modifying the neutralization rate of the selected superabsorbent material, or by modifying or otherwise controlling the chemical mechanism employed to produce the neutralization of the selected superabsorbent.

Additional aspects of determining the absorbency under load (AUL) of a superabsorbent are described in U.S. Pat. No. 5,550,189 issued Aug. 26, 1996 to J. Qin et al. and entitled MODIFIED POLYSACCHARIDES HAVING IMPROVED ABSORBENT PROPERTIES AND PROCESS FOR THE PREPARATION THEREOF; and in U.S. patent application Ser. No. 621,390 of M. Melius et al. filed Mar. 25, 1996 and entitled ABSORBENT COMPOSITE. The entire disclosures of these documents are hereby incorporated by reference in a manner that is consistent herewith.

With reference to FIGS. 2 and 2A, the representatively shown first layer region 48 can include a controlled-rate superabsorbent, and a high bulk wood pulp fiber or other woven or nonwoven fibrous material with pore size distributions which allow for a rapid uptake of liquid while maintaining the liquid within the structure until it can be absorbed by the relatively outward layer region or layer regions of the absorbent. The components in the first layer region portion 48 can be positioned to substantially cover the appointed target area 52 of the product, the area where liquids, such as urine, are introduced into the absorbent structure. Accordingly, the first layer region 48 can operatively be an appointed intake layer region of the absorbent core. The shape of the layer region 48 can be rectangular, non-rectangular or irregular in shape, but desirably will not be larger than the underlying layer region, such as the second layer region 50. In desired aspects of the invention, the first layer region will be smaller than the underlying, second layer region. For example, a substantial entirety of the first primary layer region may be contained within a zone which begins at a laterally extending line positioned about 7% of the core length inboard from said front-most edge of the absorbent core and extends to a laterally extending line positioned about 62% of the core length inboard from said front-most edge of the absorbent core. In addition, the longitudinally extending side edges of the first primary layer region may be substantially coterminous with the corresponding side edges of the second primary layer region.

Further examples of alternative absorbent configurations are representatively shown in FIGS. 3 through 6. In particular aspects of the invention, the first layer region 48 may include a composite structure having a plurality of component sub-layer portions.

Figure 3:
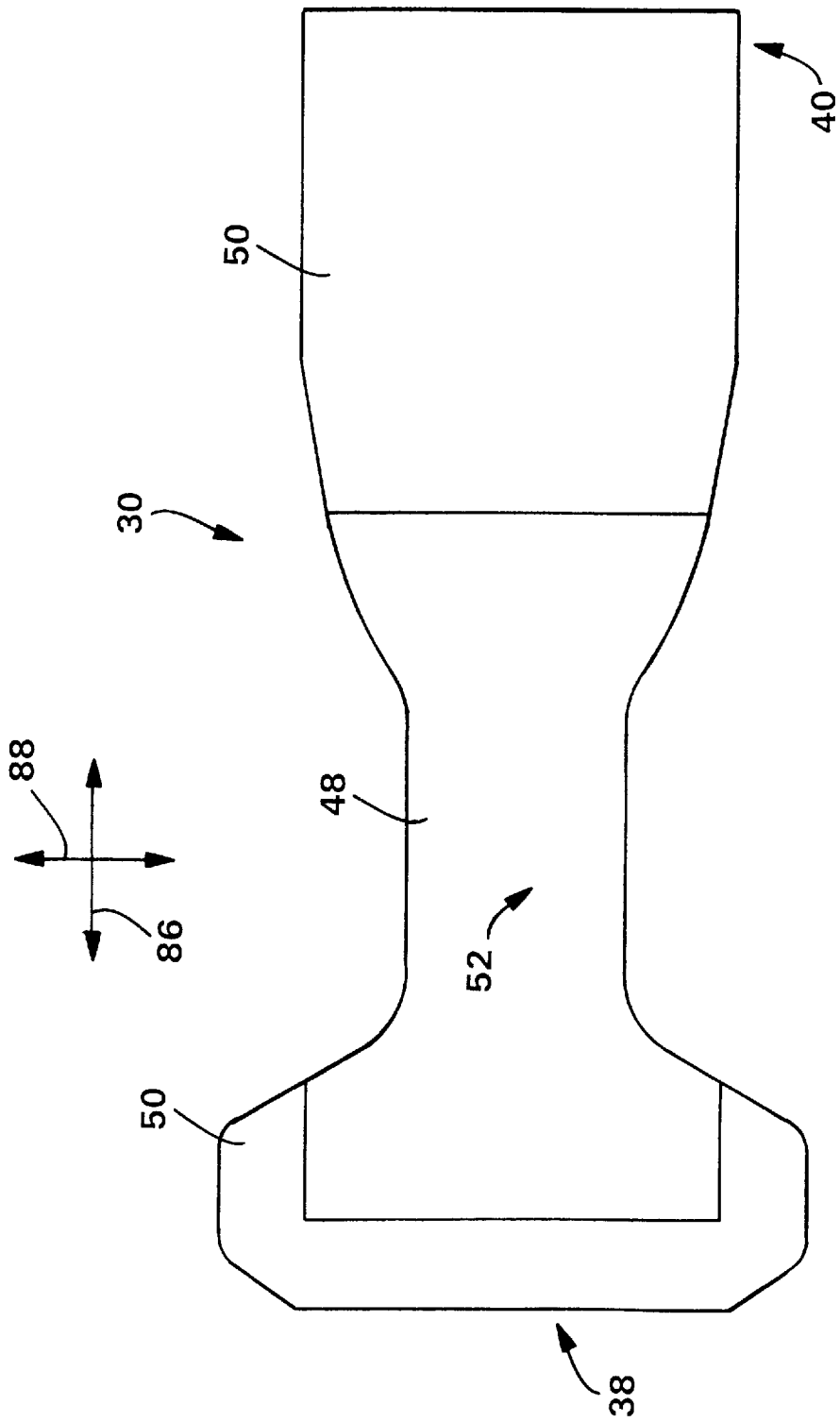
FIG. 3 top view of another absorbent core structure of the invention having a first, top layer region which extends over a medial portion of the total area of the absorbent core, and a second, bottom layer region which extends over substantially the entire area of the absorbent core, where the second layer region has a non-uniform, zoned basis weight distribution with a relatively greater basis weight at its longitudinally opposed end portions to provide a longitudinal reverse zoning of the lower layer.
Figure 3A:
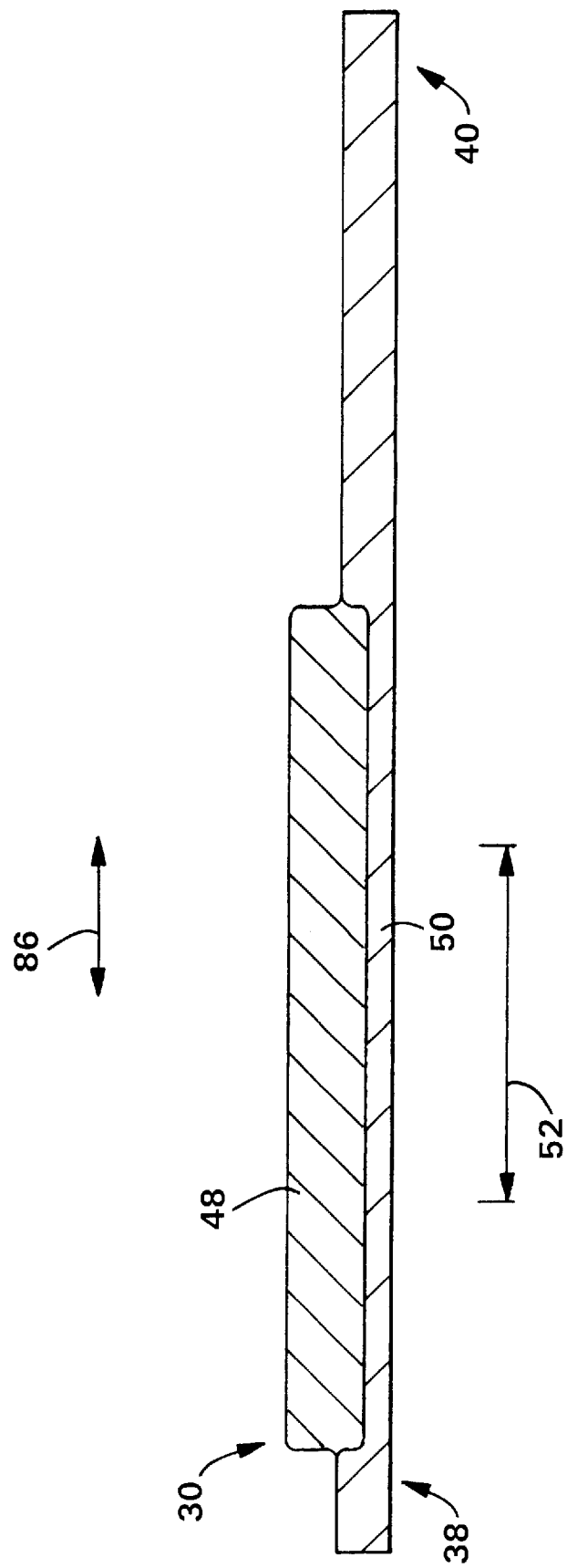
FIG. 3A representatively shows a longitudinal cross-sectional view of the absorbent core of FIG. 3, wherein a selected medial portion of the second layer region has a basis weight which is lower than that of the adjacent, longitudinally opposed end portions of the second layer to provide a reversed zoned basis weight of the second layer in the target area.

FIGS. 3 and 3A representatively show a top view of an absorbent core structure having a first, top layer region 48 which extends over a medial portion of the total area of the absorbent core 30, and a second, bottom layer region 50 which extends over substantially the entire area of the absorbent core. The second layer region 50 has a non-uniform, zoned basis weight distribution with a relatively greater basis weight at its longitudinally opposed end portions to provide a longitudinal, reverse zoning of the lower, second layer region, particularly in the target area. The selected medial portion of the second layer region 50 can also have a basis weight which is lower than that of the adjacent, overlying first layer region 48, to provide a reversed zoned thickness in the target area. At least in the crotch region of the absorbent core 30, the lateral side edges of the top layer region 48 are substantially coterminous with the side edges of the second layer region 50. Each of the longitudinal end edges of the first layer region 48 are spaced inboard from the corresponding end edges of the second layer region 50.

Figure 4:
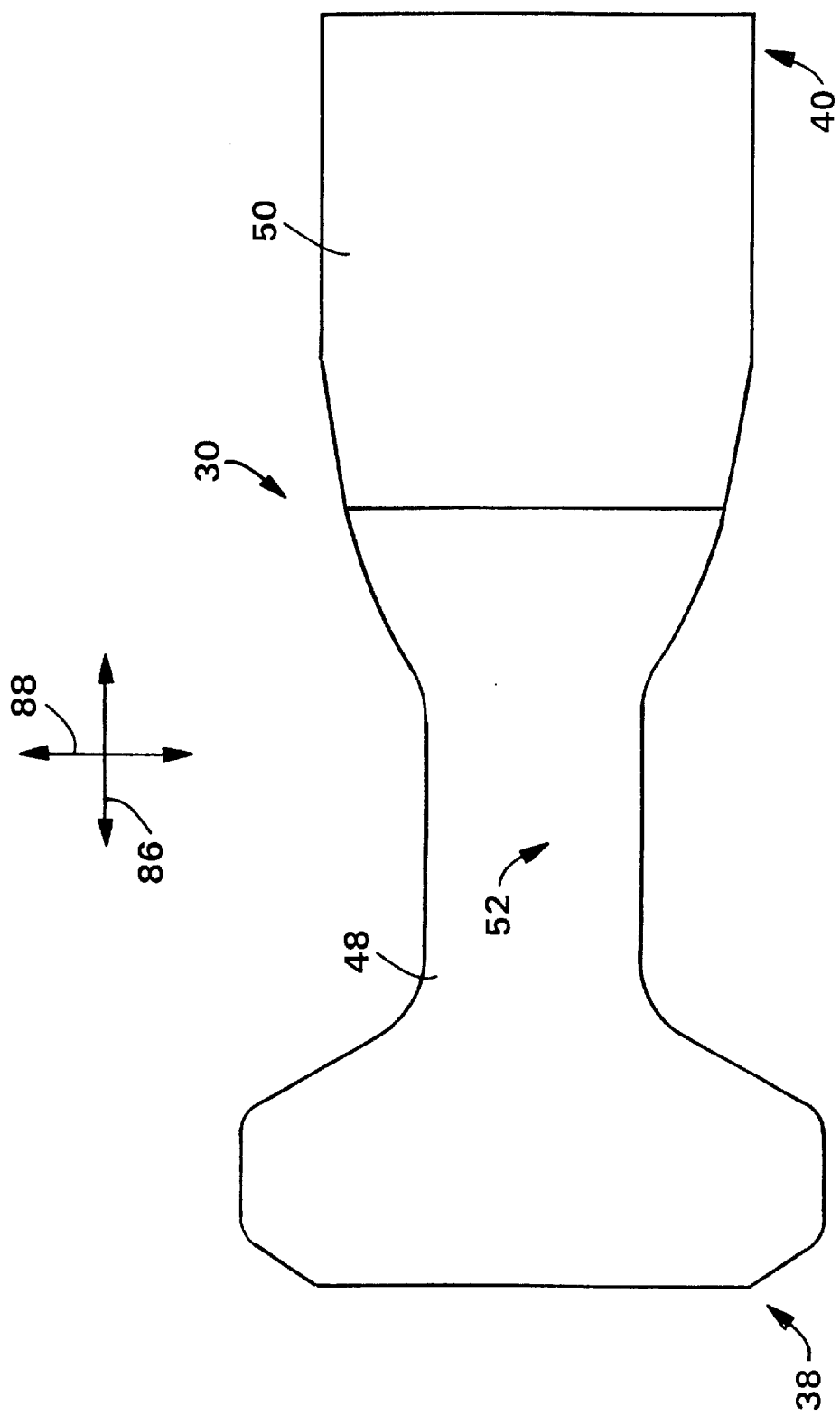
FIG. 4 representatively shows a top view of another absorbent core structure having a top layer region which covers an entire front portion of the bottom layer region, but covers less than the entire back portion of the bottom layer region.

FIGS. 4 and 4A representatively show an absorbent core structure having a top layer region 48 which covers an entire front or first portion of the bottom layer region 50, but covers less than the entire back or second portion of the bottom layer region. The lateral side edges and at least one longitudinal end edge of the first layer 48 are substantially coterminous with the lateral side edges and at least one longitudinal end edge of the second layer region 50. In the shown configuration, at least one longitudinal end edge of the first layer region 48 is spaced inboard from a corresponding end edge of the second layer region 50.

Figure 5:
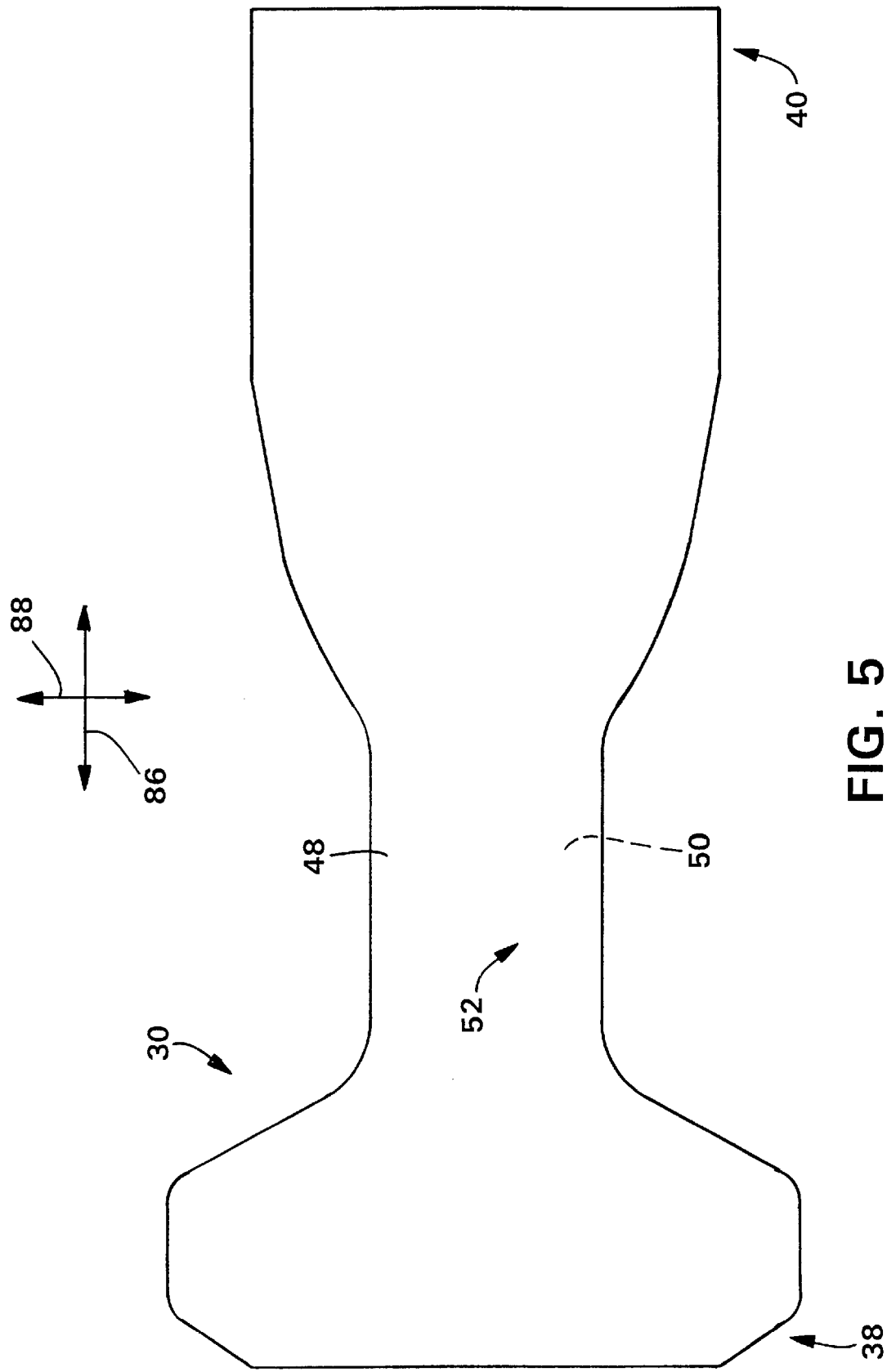
FIG. 5 top view of another absorbent core structure having a top layer region which entirely covers a bottom layer region.
Figure 5A:
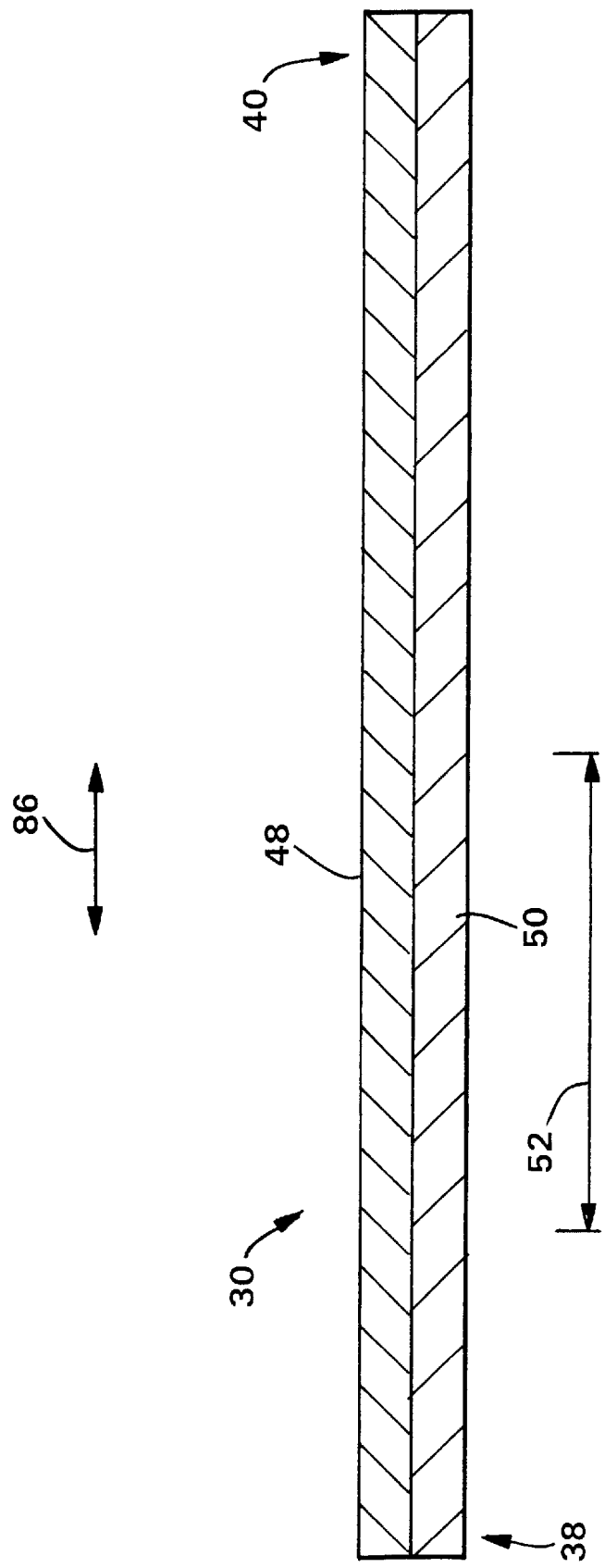
FIG. 5A representatively shows a longitudinal cross-sectional view of the absorbent core of FIG. 5.

FIGS. 5 and 5A representatively show an absorbent core structure having a top layer region which entirely covers a bottom layer region. While the shown configuration has a first layer region 48 and a second layer region 50 with substantially the same thicknesses and basis weights, the first and second layer regions may alternatively have different thicknesses and basis weights, as well as other differences in structure.

Figure 6:
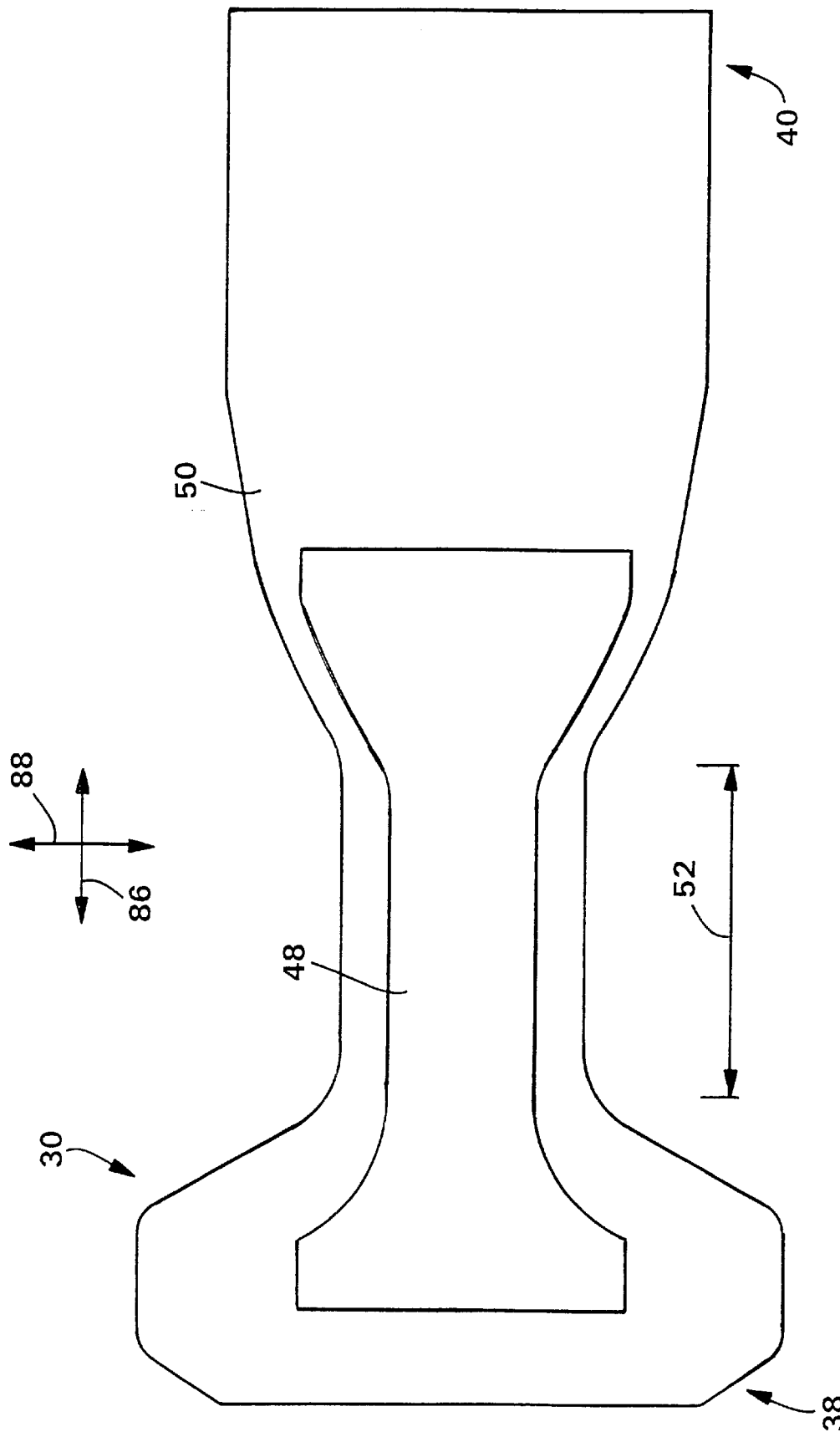
FIG. 6 representatively shows a top view of another absorbent core with a top layer region which has both a lesser, narrower lateral dimension and a lesser, shorter longitudinal dimension than the bottom layer region.

FIG. 6 representatively shows a top view of another absorbent core with a top layer region which has both a lesser, narrower lateral dimension and a lesser, shorter longitudinal dimension than the bottom layer region. In the shown configuration, for example, substantially the entire outer edge perimeter of the first layer region 48 is spaced inboard from substantially the entire outer edge perimeter of the second layer region 50.

In the various configurations of the invention, the controlled-rate superabsorbent can be configured to help regulate the rate of liquid storage in the various layer regions of the absorbent system. The controlled-rate superabsorbent can provide a rate control of liquid storage in an absorbent solely as a result of the presence of the controlled-rate superabsorbent material (SAM), or in combination of the superabsorbent with other materials to provide a controlled-rate superabsorbent composite. A controlled-rate superabsorbent or a superabsorbent composite material employing the controlled-rate superabsorbent can be used as an absorbent layer region in a multilayer region absorbent, particularly when the controlled-rate superabsorbent or the controlled-rate superabsorbent composite material is selectively configured to promote preferential saturation of one or more of the other layer regions in the multilayer absorbent core during in-use conditions. By using a combination of the high bulk fibers and the controlled-rate superabsorbent, the saturation in the first layer region 48 can be maintained at a saturation level which is lower than that of the other absorbent layer regions, resulting in higher void volume and permeability in the first layer region 48, and providing desired levels of the Flow Conductance Value.

The composite composed of high bulk fiber, particularly pulp fiber, and superabsorbent may also be modified by introducing a stabilizing agent to the composite material. The structure stabilization can be employed to maintain or minimize changes to the structure of a particular material or to the structure of the composite of materials when exposed to external or internal forces. The structure stabilization mechanism may benefit any layer region in the multiple layer-region absorbent by helping to maintain the layer region's structure when it is exposed to forces applied during in-use conditions for the products which incorporate the multiple layer absorbent core. This will help the layer region maintain its intended function, whether that be liquid intake (void volume generation), liquid storage, liquid distribution, or some combination of these three functions. Various types of suitable material technologies may be employed to stabilize absorbent structures. For example, the stabilization may occur either in the form of chemical stabilization, such as with Kymene or another cross-linking agent, or by the introduction of thermoplastic binder fibers or the like.

In the various aspects of the invention, the upper layer region 48 may be composed of a fibrous material based on a woven or nonwoven technology. As in the previous aspects of the invention, these materials will be configured to provide maximum void volume and permeability while maintaining enough capillary tension to control the movement of the liquid and not allow leakage to occur. For example, the absorbent cores of the present invention could incorporate nonwoven materials as functional components for the top layer region 48. Bonded carded webs are examples of particular fibrous materials that could be configured to provide an adequate balance of permeability and capillarity. Through the selection of staple fiber options, one can create a composite structure that will preferentially saturate the bottom absorbent layer 50. This can be done either through physical structuring of the top layer, controlled surface chemistry or both. The porosity of fibrous structures can be determined by the specific fibers and fiber sizes selected. Fiber selection can also impact the capillarity of the material.

Suitable carded structures have been produced from a variety of fiber types and from an assortment of fiber sizes. Fibers can be produced from both synthetic and naturally occurring materials. Desirably, the fibers for the first layer 48 would be very wettable, and natural cellulosic materials such as rayon or cotton may be employed. Synthetic fibers such as polyester and polyamide offer limited wettability which could be enhanced with hydrophilic finishes or treatments. While fiber diameters of a fairly wide range occur in carded nonwovens the desired structure would contain fibers with equivalent diameters less than 25 microns. A carded material for the first layer 48 could be produced in a weight range from about 50 to 200 grams per square meter (gsm) at a density of about 0.03 g/cc or less. The density of the fibrous material will ultimately depend upon the method used to bond or stabilize the web.

Carded webs can be stabilized through various methods. Incorporation of thermoplastic staple fibers is used in some cases so that the structure might be bonded using heat and pressure. Proper application of heat and pressure in thermal bonding can result in a structure that is stabilized with very specific permeability and capillarity. Carded structures can also be stabilized using chemical resins or adhesives. Again, selection of the specific resin or adhesive, add-on amounts and curing will facilitate control of the final web properties which impact permeability and capillarity. Wettability can be impacted by the choice of chemical resin system for bonding. Carded structures can be mechanically stabilized using water, needling, air or other means to entangle fibers. Again, these processes can be controlled in such a way that physical attributes of the material are as desired.

Particular aspects of the invention can incorporate a spunbonded fabric with properties similar to that described above. Other aspects of the invention may also include a selected zoning of the fiber size, basis weight, or other features of the material to provide desired performance attributes. In addition to carded fibrous webs and meltspun fibrous webs, airlaid fibrous materials may also be used.

The component materials in the first layer region 48 can be in the amounts, basis weights, densities, etc. that are described below. Typical basis weights of the region of the absorbent core structure which is positioned in a front half-portion of the article can be from about 750 gsm to about 950 gsm. The first layer region, as described above, can provide anywhere from about 25% to about 75% of the overall, composite basis weight in those areas where the first layer is present. This ratio is highly dependent on the materials being used and their relative efficiencies. The materials in which superabsorbent materials are used in combination with fluff and/or some staple fibers usually will have an initial density of 0.1 g/cc to 0.3 g/cc. The materials which are synthetic based, carded webs and melt-spun webs, can have a density from about 0.015 g/cc to 0.3 g/cc, and will desirably have a density of about 0.2 g/cc. Webs of synthetic fibers will have fiber sizes typically less than 3 denier and preferentially from 1–2 denier and will be treated to exhibit a low contact angle with water through several wettings. The treatment desirably does not reduce the surface tension of the liquid which passes through the fibrous web.

Other nonwoven structures may also be suitable for use as the upper layer region 48 in absorbent system of the invention. A proper balance of the capacity and capillarity of the lower layer region can ensure preferential saturation of the lower layer region over multiple insults. One can envision using a different lower layer region which has better distribution capability. This would aid in the desorption of the nonwoven upper layer region and should improve performance after the second insult.

Desired aspects of the invention can provide a Liquid Wicking Value which is at least the value of about 38%. Other desired aspects can provide a Liquid Wicking Value of at least about 24%, and a Flow Conductance Value of at least about $4 \times 10^{-6}$ cm$^3$. In still other aspects, the invention can have a Combined Conductance-Wicking Value (C) which is at least about $14 \times 10^{-6}$ cm$^3$.

The desired combinations of Flow Conductance and Wicking Values can provide an advantageous balance of liquid handling characteristics. In particular, the combinations can provide a desired balance of a rapid intake of the liquid along with a rapid transport of the absorbed liquid away from the intake-target area to more remote areas of the absorbent structure. Conventional structures have not provided the desired combination of properties. Accordingly, structures which have provided a desired rapid intake have not provided a sufficiently rapid transport of the absorbed liquid away from the intake area, and structures which have provided a desired rapid transport of the absorbed liquid away from the intake area have not provided a sufficiently rapid intake of the liquid. As a result, the can be a premature, excessive saturation of the absorbent target area, or an excessive pooling of liquid against the wearer's skin.

In particular aspects of the invention, the first layer region 48 can be a top, bodyside layer which can typically extend over a longitudinally medial section of the overall core area, but may optionally extend over the entire core area, if desired. The top layer typically is the layer which is optimized for intake performance and may or may not provide desired levels of liquid wicking or distribution performance. The first layer region typically can have a minimum basis weight of not less than about 100 gsm, and desirably can have a basis weight of not less than about 300 gsm. In further aspects, the first layer region typically can have a maximum basis weight of not more than about 700 gsm, and desirably has a basis weight of not more than about 600 gsm.

The first layer portion typically includes a minimum of not less than about 50% fibrous material by weight (wt %), and desirably includes not less than about 60% fibrous material. In other aspects, first layer portion typically can include a maximum of not more than about 80% fibrous material, and desirably can include not more than about 70% fibrous material. The fibrous material may be natural or synthetic in nature. The fibrous material can have a minimum fiber size, particularly a fiber diameter, of at least about 4 microns ($\mu$m), and desirably has a fiber size of at least about 10 microns. In further aspects, fibrous material can have a maximum fiber size of not more about 20 microns, and desirably has a fiber size of not more than about 15 microns. The fibers can exhibit a water contact angle of not more than about 65 degrees.

The first layer portion can also contain a minimum of not less than about 20% of superabsorbent material by weight, and desirably contains not less than about 30% superabsorbent. In additional aspects, the first layer portion can include a maximum of not more than about 50% superabsorbent material, and desirably can include not more than about 40% superabsorbent. The superabsorbent material can have a minimum, dry particle size of not less than about 110 microns, and desirably has a dry particle size of not less than about 300 microns. In other aspects the superabsorbent material can have a maximum, dry particle size of not more than about 1000 microns, and desirably can have a dry particle size of not more than about 700 microns. The superabsorbent material can also have a MAUL value of not less than about 20 g/g, and desirably can have a MAUL value of not less than about 25 g/g. Additionally, the MAUL value can be up to about 30 g/g, or more to provide improved benefits. In still other aspects, the superabsorbent material can have a Tau value of at least about 0.8 minutes, and can have a Tau value of up to about 40 minutes.

The first layer region 48 can typically have a minimum average density of at least about 0.03 g/cc, and desirably has a density of at least about 0.05 g/cc. In other aspects, the first layer region can have a maximum average density of not more than about 0.4 g/cc, and desirably can have a density of not more than about 0.2 g/cc. The first layer region includes any tissue layers which are used to hold together the materials positioned in the first layer region or which act as a carrier mechanism. For example, several layers of tissue may be employed to hold superabsorbent material which is laminated between the tissue layers.

The various configurations of the invention can include any operative intake material in the selected layers of the absorbent structure. Examples of suitable intake materials can include the materials described in U.S. patent application Ser. No. 754,414 entitled MULTIFUNCTIONAL ABSORBENT MATERIAL AND PRODUCTS MADE THEREFROM, by R. Anderson et al., and filed Nov. 22, 1996; and in U.S. Provisional Patent Application Ser. No. 068,534 entitled PULP AND SUPERABSORBENT COMPOSITE FOR IMPROVED INTAKE PERFORMANCE, by L. H. Sawyer et al., and filed Dec. 23, 1997. The entire disclosures of these documents are incorporated herein by reference in a manner that is consistent herewith.

With reference to FIGS. 2 and 2A, the second layer region portion 50 can include a mass or matrix of hydrophilic fibers, such as wood pulp fibers, and a selected quantity of superabsorbent gelling material, such as Coosa 1654 wood pulp and Stockhausen Favor 880 superabsorbent. These materials will typically be blended or otherwise combined such that about 20–80 wt % of the composite is composed of superabsorbent particles. Modifications of this material may also be made to provide improved product performance. These modifications can include the use of modified pulp fibers to generate improvements in the distribution of liquid, or the use of a stabilization technique to control the structure and generate improved wicking performance. Potential methods of stabilization include, but are not limited to, the use of a binder material, such as Kymene or some other cross-linking agent, or the introduction of heat activated binder fibers. Structure stabilization is a technology that is used to maintain the structure or minimize changes to the structure of a material or a composite of materials when the materials are exposed to external or internal forces. Various techniques, such as the incorporation of thermoplastic binder fibers, chemical cross-linking agents (such as Kymene), and the like, as well as combinations thereof, may be employed to stabilize the absorbent structures.

Any material which is operatively configured with the ability to provide improved distribution of liquid away from the target area can provide the desired functional results. These materials can be composed of a laminate which includes superabsorbent particles and at least one fibrous web which is particularly configured to exhibit an improved wicking flux performance. Suitable arrangements of the second layer region 50 can include, but are not limited to, laminations of particulate or fibrous superabsorbent webs with cellulosic tissue materials, or any other stabilized, fibrous web. Other suitable fibrous webs may include wet laid tissue, airlaid materials incorporating staple synthetic and natural fibers, or treated meltblown webs, as well as the types of fibrous webs employed to construct the first layer region 48. Another class of materials which can be used to provide improved functionality are laminates of superabsorbent particles or fibrous webs and wettable, open cell foams.

The second layer region 50 can be positioned in various suitable configurations. For example, the second layer region can be in the form of a separately provided absorbent pad which is positioned immediately adjacent to the first layer region 48. The second layer region 50 is desirably in a substantially direct contact with the first layer region 48, but may alternatively be positioned spaced from the upper layer region with one or more layer regions of selected material interposed between the first layer region 48 and the second layer region 50. In particular aspects of the invention, the second layer region 50 is configured to allow for a maximum utilization of the absorbent to the incoming liquid while also maintaining product attributes pleasing to the consumer.

In further aspects, the second primary layer region can have a longitudinal extent which is greater than a longitudinal extent of said first primary layer region. Additionally, the second primary layer region can have a lateral extent which is substantially coterminous with said first primary layer region. Alternative configurations can include a second primary layer region which has a lateral extent which is less than a lateral extent of said first primary layer region. For example, the lateral extent of at least a portion of the second primary layer region can be not less than about 30% of the lateral extent of a correspondingly adjacent portion of the first primary layer region. Other configurations can include a second primary layer region which has a lateral extent which is greater than a lateral extent of the first primary layer region. For example, the lateral extent of at least a portion of the first primary layer region can be not less than about 30% of the lateral extent of a correspondingly adjacent portion of the second primary layer region.

The component materials in the second layer region 50 can be provided in various operative amounts, basis weights, densities, etc. For example, the second primary layer region may have a substantially uniform basis weight, or desirably, a selected nonuniform basis weight. Additionally, the second layer region 50 can constitute about 25%–100% of the overall, composite basis weight of the absorbent core structure at any one location, and may typically have a density in the range of about 0.1 g/cc to 0.3 g/cc. In still other aspects, the second layer region portion 50 may include a plurality of two or more component sub-layer regions, wherein each of the component sub-layer regions has a selected combination of physical and functional characteristics.

In particular aspects of the invention, at least one of the layer regions of the absorbent core 30 is a distributing layer which can provide a Liquid Wicking Value of not less than about 16%. In addition, the distributing layer has a perimeter boundary and area which extend beyond and past the appointed target region 52 of the absorbent composite. The distributing layer can advantageously provide particular important functions. A first function includes the retention and movement of liquid away from the target area, and a second function is to provide enough short term (during liquid insult) superabsorbent capacity to make up for the shortfall in void volume associated with thin product executions. Structural elements of this layer region include the SAP content, the component basis weights, and the component densities. Examples of materials with high liquid wicking performance are described in U.S. Pat. No. 5,350,370 entitled "HIGH S WICKING LIQUID ABSORBENT COMPOSITE", and issued Sep. 27, 1995 to D. M. Jackson et al., the entire disclosure of which is incorporated herein by reference in a manner that is consistent herewith.

The second layer region 50 can provide a bottom layer, and can typically extend over the entire area of the of the overall absorbent core 30. The second layer region 50 is typically designed to provide the bulk of the distribution or wicking ability of the absorbent core, and therefore will typically extend beyond and past the terminal edges of the area covered by the first layer region 48. Within the target area 52 of the absorbent core, the second layer region typically can have a basis weight of not less than about 100 gsm, and desirably can have a basis weight of not less than about 150 gsm. In further aspects, the target area of the second layer region typically can have a basis weight of not more than about 700 gsm, and desirably has a basis weight of not more than about 250 gsm. In non-target portions which are outside of the target area of the second layer region 50, the second layer region typically can have a basis weight of not less than about 300 gsm, and desirably can have a basis weight of not less than about 450 gsm. In further aspects, the non-target portions of the second layer region which are outside the target area can typically have a basis weight of not more than about 800 gsm, and desirably has a basis weight of not more than about 550 gsm.

The second layer portion typically includes not less than about 50% fibrous material by weight, and desirably includes not less than about 60% fibrous material. In other aspects, second layer portion typically can include not more than about 95% fibrous material, and desirably can include not more than about 70% fibrous material. The fibrous material may be natural or synthetic in nature. The fibrous material can have a fiber size, particularly a fiber diameter, of at least about 4 microns, and desirably has a fiber size of at least about 10 microns. In further aspects, fibrous material can have a fiber size of not more about 20 microns, and desirably has a fiber size of not more than about 15 microns. In addition, the fibrous material can have a contact angle with water of not more than about 65 degrees, and desirably has a contact angle with water of not more than about 50 degrees.

The second layer portion can also contain not less than about 5% of superabsorbent material, by weight, and desirably contains not less than about 15% superabsorbent. In additional aspects, the second layer portion can include not more than about 50% superabsorbent material, and desirably can include not more than about 40% superabsorbent. The superabsorbent material can have a dry particle size of not less than about 110 microns, and desirably has a dry particle size of not less than about 300 microns. In other aspects the superabsorbent material can have a dry particle size of not more than about 1000 microns, and desirably can have a dry particle size of not more than about 700 microns. The superabsorbent material can also have a MAUL value of not less than about 20 g/g, and desirably can have a MAUL value of not less than about 25 g/g. Additionally, the MAUL value can be up to about 30 g/g, or more to provide improved benefits. In still other aspects, the superabsorbent material can have a Tau value of at least about 0.67 minutes, and can desirably have a Tau value of at least about 2 minutes.

Advantageous configurations of the invention can include a second layer region 50 which has a Liquid Wicking Value of at least about 36% and contains a superabsorbent having a Tau value of not less than about 0.4 minutes. Other advantageous arrangements can include a second layer region which has a Liquid Wicking Value of at least about 16% and contains a superabsorbent having a Tau value of not less than about 0.67 minutes.

In particular aspects of the invention, the superabsorbent material in the first layer region 48 is configured to have a Tau value which is about twice the Tau value of the superabsorbent located in the second layer region 50 (Tau-value-ratio of about 2:1). The Tau-value-ratio can alternatively be at least about 2.5:1, and optionally, can be at least about 3:1 to provide desired characteristics. In additional aspects, the combination of superabsorbent materials in the first and second layer regions can be configured to provide a Tau-value-ratio of up to about 10:1, and alternatively, the combination of superabsorbent materials can be configured to provide a Tau-value-ratio of up to about 40:1, or more.

The second layer region 50 can typically have an average density of at least about 0.1 g/cc, and desirably has a density of at least about 0.15 g/cc. In other aspects, the second layer region can have an average density of not more than about 0.3 g/cc, and desirably can have a density of not more than about 0.25 g/cc. In particular aspects, the average density can be about 0.2 g/cc. The second layer region includes any tissue layers which are used to hold together the materials positioned in the second layer region or which act as a carrier mechanism. For example, several layers of tissue may be employed to hold a layer of superabsorbent material which is laminated between the tissue layers.

In particular aspects of the invention, at least one of the primary layer regions includes a laminate having one or more layers of a liquid-permeable material 100 which operates as a distribution material, such as layers of an uncreped-through-air-dried (UCTAD) sheet material. For example, the sheet material may be a fibrous tissue, and desired configurations can incorporate the selected UCTAD material in the second primary layer region of the absorbent core.

Suitable UCTAD materials can provide a wicking property characterized by a liquid flux, at a height of 15 cm, which is at least 0.002 grams of liquid per minute per basis weight of 1 $g/m^2$, per 1 inch of material width. The UCTAD material has a basis weight of at least about 50 $g/m^2$, and has a density within the range of about 0.08–0.5 g/cc. Desirably, the density is within the range of about 0.1–0.3 g/cc. The permeability of the UCTAD is within the range of about 50–1000 Darcys. The UCTAD material has a dry tensile strength of at least 5000 grams of force per 1 inch of the material plied to a total basis weight of 200 $g/m^2$.

Suitable UCTAD materials are described in U.S. patent application Ser. No. 08/767,645 filed Dec. 17, 1996 by J. Dutkiewicz et al., and entitled ABSORBENT STRUCTURE FOR LIQUID DISTRIBUTION, the entire disclosure of which is incorporated by reference in a manner that is consistent herewith.

With reference to FIG. 8, the second primary layer region 50 can include a composite which includes an assembled hetergeneous plurality of sublayer sections 62 and 64. In the illustrated configuration, for example, a first sublayer section 62 can extend over an substantial entirety of the area covered by the absorbent core 30, and a pair of spaced-apart, second sublayer sections 64 are positioned adjacent a bodyside surface of the first sublayer section 62, with each of the second sublayer sections extending over a selected partial fraction of the overall surface area of the absorbent core 30. The shown configuration has the second sublayer sections 64 longitudinally spaced-apart, and as illustrated, each of the sublayer sections 64 can have an end edge which is substantially coterminous with its associated longitudinal end of the absorbent core 30. As a result, the second primary layer region 50 can have a zoned basis weight distribution, with a longitudinal medial portion having a basis weight which is lower than a basis weight of two longitudinally opposed end portions of the primary layer region 50.

In particular aspects of the invention, at least one of the sublayer sections can include a laminate having one or more layers of uncreped-through-air-dried (UCTAD) sheet material, such as UCTAD tissue. For example, desired configurations can include a first sublayer region 62 of the absorbent core wherein at least a cooperating pair of layers of UCTAD sheet material are constructed and arranged to sandwich a distributed layer of superabsorbent particles 102 therebetween. Additional layers of distribution material, such as additional layers of UCTAD sheet material, may be employed to further sandwich the layer of superabsorbent particles 102 within the first sublayer 62, as representatively shown in FIG. 8.

In other aspects, either or both of the second sublayer sections 64 can include at least a cooperating pair of layers of UCTAD sheet material are constructed and arranged to sandwich a distributed layer of superabsorbent particles therebetween. Additional layers of distribution material, such as additional layers of the UCTAD sheet material, may be employed to further sandwich the layer of superabsorbent particles therebetween within the second sublayers 64.

With reference to FIG. 9, the second primary layer region 50 can alternatively include a composite wherein the basis weight distribution of the superabsorbent particles is selectively zoned to provide a varying basis weight, particularly along the longitudinal direction of the second primary layer region 50. As a result, the second primary layer region 50 can have a zoned basis weight distribution of superabsorbent, with a longitudinal middle portion of the layer region 50 having a basis weight of superabsorbent which is lower than a basis weight of superabsorbent distributed at the two longitudinally opposed, end portions of the second primary layer region 50. Further descriptions of the various configurations of the invention are provided in U.S. patent application Ser. No. 09/519,045 of R. Everett et al., entitled LAYERED ABSORBENT STRUCTURE, and filed Mar. 3, 2000; U.S. patent application Ser. No. 09/519,381 of R. Everett et al., entitled LAYERED ABSORBENT STRUCTURE WITH A ZONED BASIS WEIGHT, and filed Mar. 3, 2000; and U.S. patent application Ser. No. 09/518,756 of R. Everett et al., entitled LAYERED ABSORBENT STRUCTURE WITH A HETEROGENEOUS LAYER REGION, and filed Mar. 3, 2000. The entire disclosures of each of these documents are incorporated herein by reference in a manner that is consistent herewith.

With reference again to FIG. 1, the leg elastic members 34 are located in the lateral side margins 110 of the diaper, and are arranged to draw and hold the diaper 20 against the legs of the wearer. The elastic members are secured to diaper 20 in an elastically contractible condition so that in a normal under strain configuration, the elastic members effectively contract against diaper 20. The elastic members can be secured in an elastically contractible condition in at least two ways, for example, the elastic members may be stretched and secured while diaper 20 is in an uncontracted condition. Alternatively, diaper 20 may be contracted, for example, by pleating, and the elastic members secured and connected to diaper 20 while the elastic members are in their relaxed or unstretched condition. Still other mechanisms, such as heat-shrink elastic material, may be used to gather the garment.

In the embodiment illustrated in FIG. 1, the leg elastic members 34 extend essentially along the complete length of the intermediate crotch region 42 of the diaper 20. Alternatively, elastic members 34 may extend the entire length of the diaper 20, or any other length suitable providing the arrangement of elastically contractible lines desired for the particular diaper design.

Elastic members 34 may have any of a multitude of configurations. For example, the width of the individual elastic members 34 may be varied from about 0.25 millimeters (about 0.01 inch) to about 25 millimeters (about 1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 20 with sprayed or swirled patterns of an adhesive, such as a hotmelt, pressure-sensitive adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 20 can include a waist elastic 32 positioned in the longitudinal margins of either or both of front waistband 38 and rear waistband 40. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

The diaper 20 can also include a pair of elasticized containment flaps 82 which extend generally length-wise along the longitudinal direction 86 of the diaper. The containment flaps are typically positioned laterally inboard from leg elastics 34, and substantially symmetrically placed on each side of the lengthwise, longitudinal centerline of the diaper. In the illustrated arrangements, each containment flap 82 has a substantially fixed edge portion 81 and a substantially moveable edge portion 83, and is operably elasticized to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT, which issued as U.S. Pat. No. 5,562,650, the disclosure of which is hereby incorporated by reference in a manner that is consistent herewith.

In optional, alternative configurations of the invention, diaper 20 may include elasticized waist flaps, such as those described in U.S. Pat. No. 4,753,646 issued Jun. 28, 1988, to K. Enloe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18, 1995, the entire disclosures of which are hereby incorporated by reference in a manner that is consistent herewith. Similar to the construction of the containment flaps, the waist flaps may be composed of a wettable or non-wettable material, as desired. The waist flap material may be substantially liquid-impermeable, permeable to only gas, or permeable to both gas and liquid.

To provide a refastenable fastening system, diaper 20 can include an appointed landing zone 78 (e.g. FIG. 1A), which can provide an operable target area for receiving a releasable attachment of the fastener tabs 44 thereon. In particular embodiments of the invention, the landing zone patch can be positioned on the outward surface of backsheet layer 22 and is located on the front waistband portion 38 of the diaper. The fastening mechanism between the landing zone and the fastener tabs 44 may be adhesive, cohesive, mechanical or combinations thereof. A configuration which employs a releasable, interengaging mechanical fastening system can, for example, locate a first portion of the mechanical fastener on the landing zone 78 and a second, cooperating portion of the mechanical fastener on the fastener tab 44. For example, with a hook-and-loop fastener, the hook material 46 can be operably connected to the fastener tabs 44 and the loop material 80 can be operably connected to the landing zone 78. Alternatively, the loop material can be operably connected to the fastener tabs 44 and the hook material can be operably connected to the landing zone.

In the various embodiments of the invention, a tape fastener tab 44 can be located at either or both of lateral end regions 116 and 118 of either or both of the waistbands 38 and 40. The representatively shown embodiment, for example, has the fasteners tabs 44 located at the distal side edges of the rear waistband 40. In addition the backsheet layer 22 can have an appointed fastener landing zone 78 disposed on an outward surface of the backsheet layer.

With reference to FIG. 1, for example, the article can include a system of side panel members 90. In particular arrangements, each side panel member 90 extends laterally from the opposed lateral ends of at least one waistband portion of backsheet 22, such as the representatively shown rear waistband portion 40, to provide terminal side sections of the article. In addition, each side panel can substantially span from a laterally extending, terminal waistband edge 106 to approximately the location of its associated and corresponding leg opening section of the diaper. Diaper 20, for example, has a laterally opposed pair of leg openings formed by appointed, medial sections of the shown pair of longitudinally extending, side edge regions 110 (FIG. 1). Each side panel can span a longitudinal distance of at least about 4 cm, optionally may span a longitudinal distance of at least about 5 cm, and alternatively may span a distance of at least about 6 cm to provide improved fit.

In the various configurations of the invention, the side panels may be integrally formed with a selected diaper component. For example, side panels 90 can be integrally formed from the layer of material which provides backsheet layer 22, or may be integrally formed from the material employed to provide topsheet 24. In alternative configurations, the side panels 90 may be provided by one or more separate members that are connected and assembled to the backsheet 22, to the topsheet 24, in between the backsheet and topsheet, and in various fixedly attached combinations of such assemblies.

In particular aspects of the invention, each of the side panels 90 may be formed from a separately provided piece of material which is then suitably assembled and attached to the selected front and/or rear waistband portion of the diaper article. In the illustrated embodiments of the invention, for example, each side panel 90 is attached to the rear waistband portion of backsheet 22 along a side panel attachment zone 94, and can be operably attached to either or both of the backsheet and topsheet components of the article. The shown configurations have the inboard, attachment zone region of each side panel overlapped and laminated with its corresponding, lateral end edge region of the waistband section of the article. The side panels extend laterally to form a pair of opposed waist-flap sections of the diaper, and are attached with suitable connecting means, such as adhesive bonding, thermal bonding, ultrasonic bonding, clips, staples, sewing or the like. Desirably, the side panels extend laterally beyond the terminal side edges of the backsheet layer and topsheet layer at the attached waistband section of the article. The side panels 90 may be composed of a substantially non-elastomeric material, such as polymer films, woven fabrics, nonwoven fabrics or the like, as well as combinations thereof. In particular aspects of the invention, side panels 90 are composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 88. For example, suitable meltblown elastomeric fibrous webs for forming side panels 90 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the side panels 90 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Where the side panels 90 are composed of a material which has been elasticized or otherwise constructed to be elastomerically stretchable, the elastomeric side panels can desirably provide an elongation at peak load of at least about 30 percent when subjected to a tensile force load of 0.33 pounds per lineal inch of the sample dimension that is measured perpendicular to the direction of the applied load (about 0.58 Newtons/cm). Alternatively, the elastomeric side panel material can provide an elongation of at least about 100%, and optionally can provide an elongation of at least about 300% to provide improved performance.

Each of the side panels 90 extends laterally from opposed lateral ends of at least one waistband section of the diaper 20. In the shown embodiment, each side panel extends laterally from opposed lateral ends of the rear waistband section of the backsheet 22. Each of the side panels includes a relatively outboard, terminal free end region 92 which has a longitudinally extending length dimension. Each side panel also has a laterally extending width dimension and a base region attachment zone 94 which has a lapped, construction bond attachment to either or both of the topsheet and backsheet layers. The side panels may have a tapered or otherwise contoured shape in which the base length of the side panel attachment zone 94 is larger than the length of the relatively outboard distal end region 92. Alternatively, the length of the attachment zone 94 may be smaller than the length of the relatively outboard distal end region 92. Optionally, the side panels may have a substantially rectangular shape or a substantially trapezoidal shape.

A stress beam section 98 can be constructed on each of the side panels 90 along its outboard, free end region 92 to more evenly distribute tensile stresses across the side panel area. The stress beam section is configured with a relatively high stiffness value, and in desired configurations, the stress beam section extends along substantially the entire longitudinal length of the side panel outboard region 92. A fastening tab 44 can be connected to extend laterally from the stress beam section of each of the side panels 90 for securing the waistband sections of the article about a wearer during the use of the article.

Each fastening tab 44 can include a carrier layer 56 which interconnects an inboard edge region of the selected fastening component, such as the shown hook member 46, to the outboard edge region of its associated and corresponding side panel 90. The carrier layer has a laterally inboard, first side region and a laterally outboard, second side region. The first side region is laminated, or otherwise connected and affixed, to the side panel with an operable construction bond. The side panel material, the carrier layer material and the configuration of the construction bond are constructed and arranged to form the operative stress beam section 98. Optionally, an additional layer of reinforcement material may be included along the stress beam region to increase the stiffness of the beam and to further improve its ability to spread stresses along the longitudinal dimension of the side panel. The inboard region of the carrier layer 56 may have a longitudinal extent which is less than the longitudinal dimension of the outboard, free edge portion 92 of the side panel 90. Alternatively, the carrier layer 56 can have a longitudinal extent which is substantially equal to (e.g. FIG. 1) or greater than the longitudinal dimension of the outboard portion of the side panel.

The member of hook material 46 is laminated, or otherwise connected and affixed, to the outboard region of the carrier layer with an operable construction attachment. In particular, the shown hook member 46 is laminated to a inward, bodyside surface of the carrier layer with the hook elements extending generally inwardly of the article. With the illustrated arrangement, the outboard, laterally distal edge of the second carrier edge region is coterminous with the outboard, laterally distal edge of the hook member 46. Alternatively, the outboard, laterally distal edge of the second carrier edge region may be spaced laterally inboard from the terminal, laterally distal edge of the hook member 46. In either configuration, the laterally distal edge of the hook member 46 provides the laterally terminal edge of the article.

The longitudinally extending, relatively outboard edge of the side panel member 90 may be spaced from the longitudinally extending, relatively inboard edge of the selected fastening region by a carrier spacing distance. More particularly, the outboard edge of the side panel member 90 can also be spaced from the relatively inboard edge of the hook member 46 by the carrier spacing distance. The spacing distance optionally has a lateral extent which is equal to or greater than the lateral extent of the fastening region. In addition, the inwardly facing, bodyside surface of the carrier layer 56 is constructed to have a limited, mechanical interengageability with the hook elements. As a result, the fastener tab 44 can be folded along a longitudinally extending fold line to selectively locate and configure the fastening region in a storage position with the hook elements placed and held against the bodyside surface of the carrier layer 56. The level of engagement between the hook material and the carrier layer need only be enough to maintain the storage position. For example, the engagement may provide a single-peak, peel force value within the range of about 1–50 grams of force.

In particular configurations of the invention, the material of carrier layer 56 can be composed of a substantially non-elastomeric material, such as polymer films, woven fabrics, nonwoven fabrics or the like, as well as combinations thereof. Alternatively, the carrier web material may be composed of a substantially elastomeric material, such as a stretch-bonded-laminate (SBL) material, a neck-bonded-laminate (NBL) material, an elastomeric film, an elastomeric foam material, or the like, as well as combinations thereof. The elastomeric material is elastomerically stretchable at least along the lateral direction 88. For example, the carrier web material can be composed of a spunbond-meltblown-spunbond (SMS) fabric having a core of meltblown fibers sandwiched between two facing layers of spunbond fibers to provide a total composite basis weight within the range of about 50–67 g/m$^2$ (about 1.5–2 oz/yd$^2$). As another example, the carrier web material may be entirely composed of a nonwoven spunbond fabric having a basis weight within the range of about 50–67 g/m$^2$ (about 1.5–2 oz/yd$^2$).

The mechanical fasteners cooperatively employed with the various configurations of the invention can be provided by mechanical-type fasteners such as hooks, buckles, snaps, buttons and the like, which include cooperating and complementary, mechanically interlocking components. In particular aspects of the invention, the fastening means can be provided by a hook-and-loop fastener system, a mushroom-and-loop fastener system, or the like (collectively referred to as hook-and-loop fasteners). Such fastening systems generally comprise a "hook" or hook-like, male component, and a cooperating "loop" or loop-like, female component which engages and releasably interconnects with the hook component. Desirably, the interconnection is selectively releasable. Conventional systems are, for example, available under the VELCRO trademark.

Examples of suitable hook-and-loop fastening systems are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. which issued as U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer 56 are described in U.S. patent application Ser. No. 08/603,477 of A. Long et al., entitled MECHANICAL FASTENING SYSTEM WITH GRIP TAB and filed Mar. 6, 1996 which issued as U.S. Pat. No. 5,624,429, the entire disclosure of which is hereby incorporated by reference in a manner which is consistent herewith.

In a typical configuration of a hook-and-loop fastening system, the hook material member 46 is operably connected to the fastening tab 44, and the loop material 80 is employed to construct at least one cooperating landing zone 78. The landing zone, for example, can be suitably positioned on the exposed, outward-side surface of the backsheet 22. As previously mentioned, an alternative configuration of the hook-and-loop fastening system may have the loop material secured to the fastener tab 44 and may have the hook material employed to form the landing zone 78.

In particular aspects of the invention, the hook material member 46 can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mgf (milligrams-force).

Another suitable micro-hook material is distributed under the designation VELCRO CFM-29 1058, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch) and the member of hook material has a Gurley stiffness of about 12 mgf (12 Gurley Units).

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y.

In the various configurations of the invention, the loop material can be provided by a nonwoven, woven or knit fabric. For example, a suitable loop material fabric can be composed of a 2 bar, warp knit fabric of the type available from Guilford Mills, Inc., Greensboro, N.C. under the trade designation #34285, as well other of knit fabrics. Suitable loop materials are also available from the 3M Company, which has distributed a nylon woven loop under their SCOTCHMATE brand. The 3M Company has also distributed a liner-less loop web with adhesive on the backside of the web, and 3M knitted loop tape.

In particular aspects of the invention, the loop material need not be limited to a discrete landing zone patch. Instead the loop material can, for example, be provided by a substantially continuous, outer fibrous layer which is integrated to extend over substantially the total exposed surface area of a cloth-like outer cover employed with the diaper 20. The resultant, cloth-like backsheet 22 can thereby provide the loop material for an operative "fasten anywhere" mechanical fastening system. As a practical matter, the area extent of the loop material will depend on the cost of the material.

The fastening elements in the various constructions of the invention may be operably attached to its base layer by employing any one or more of the attachment mechanisms employed to construct and hold together the various other components of the article of the invention. Desirably, the fastening elements in the various fastening regions, may be integrally formed, such as by molding, co-extrusion or the like, along with the associated base layer. The base layer and the mechanical fastening elements can be formed from substantially the same polymer material, and there need not be a discrete step of attaching the fastening elements to an initially separate hook base layer. In the representatively shown configurations of the primary fastening region, for example, the hook elements can be integrally formed simultaneously with the hook base layer by coextruding the base layer and hook elements from substantially the same polymer material.

It should be readily appreciated that the strength of the attachment or other interconnection between the base layer and the attached fastening component should be greater than the peak force required to remove the fastener tab 44 from its releasable securement to the appointed landing zone of the article.

Calculation and Testing Procedures
Partial Saturation Thickness Procedure

The thickness height (h) of each layer in its partially saturated state can be determined by again using the inputs as determined above and the following procedure:

Scope

The thickness (h) of each layer region in a partially saturated state is determined.

Equipment and Materials

Glass petri dish (100×15 mm—Corning Number 3160-101—Fisher Scientific Catalog Number 08-747C).

Blood bank saline solution, such as catalogue No. 8504 Blood bank saline obtained from Stevens Scientific, a division of Cornwell Corporation, a business having offices located at Riverdale, N.J.; or a substantial equivalent.

Thickness tester with 0.05 psi (0.345 KPa) platen of 3 inch (7.62 cm) diameter.

Die cutter—3 inch (7.62 cm) diameter circle.

Weighing scale.

Laboratory timer.

Test Procedure

Die cut a 3 inch (7.62 cm) diameter sample of the material to be tested.

Calculate the saturation (grams fluid/grams sample) of the layer based on a 0.6 g/cm² saturation of the absorbent and superabsorbent mass, and employing the technique discussed in the Flow Conductance Calculation.

Weigh the dry sample and record the weight.

Calculate the amount of liquid saline solution to be added to the sample by multiplying the dry sample weight by the desired saturation level.

Dispense the calculated amount of liquid into a petri dish on flat surface to provide a uniform distribution of liquid to the sample.

Place the sample into the petri dish such that the sample remains flat. Start the timer.

After 30 minutes have elapsed, remove the sample from the petri dish.

Measure the thickness of the sample (in mm) under a restraining pressure of 0.05 psi (0.34 KPa), and record the thickness.

The values of the partial saturation thickness height (h) can the be employed in the equations employed to calculate the Flow Conductance Value for the absorbent composite system.

Flow Conductance Calculation

The Flow Conductance of the absorbent core at a liquid loading of 0.6 g/cm² of absorbent is used to reflect the intake capability of an absorbent core structure when the core is in its partially saturated state. The Flow Conductance can be described by the following equation:

$$\text{Flow Conductance Value} = K_1 h_1 + K_2 h_2 + K_3 h_3 + \ldots$$

Where:

K=the permeability of each layer at a given saturation.

h=the thickness of each layer at a given saturation.

The permeability (K) of each layer in the core can be computed as follows: Each layer in the absorbent core-is a combinations of substantially non swelling fibers and superabsorbent particles, fibers or flakes.

Expressions for the permeability of a collection of cylinders oriented randomly and for a collection of spheres are:

For cylindrical and other regular or irregular, elongated fiber shapes:

$$K = \left(\frac{0.30}{\left(\frac{SA}{V}\right)^2}\right)(1-\varepsilon)\left(\frac{\varepsilon}{1-\varepsilon}\right)^{2.5}$$

For generally spherical, and other regular or irregular particle shapes:

$$K = \left(\frac{0.3555}{\left(\frac{SA}{V}\right)^2}\right)(1-\varepsilon)\left(\frac{\varepsilon}{1-\varepsilon}\right)^{2.35}$$

where SA/V is the surface area to volume ratio of the solid portion in cm⁻¹ and the porosity, $\varepsilon$, is the ratio of the pore volume to the total volume of the entire medium. The basis for the above permeability expressions comes from Happel and Brenner, *Low Reynolds Number Hydrodynamics*, Noordhoff International Publishing (1973). Expressions of permeability for the cylinders and spheres derived in that work were fit to simpler forms, as shown above, to obtain the value of the exponent and the multiplier.

It has been observed that essentially all the liquid delivered during the first insult is imbibed by the superabsorbent before the second insult is delivered. Accordingly, for the purpose of calculating the permeability value employed in the flow conductance computations, all of the above specified liquid (0.6 g/cm²) is considered to be within the superabsorbent. Therefore, in calculating the values for porosity, $\varepsilon$, and the surface area per volume ratios for the superabsorbents, the liquid volume is included as part of the solid volume. Thus, the porosity, $\varepsilon$, of the material is given by:

$$\varepsilon = 1 - [(\text{solid volume} + \text{liquid volume})/(\text{total volume occupied by wetted sample})];$$

where the total volume occupied by the wetted sample is determined by the area of the sample multiplied by the thickness of the sample. Thickness of the sample can be determined by Partial Saturation Thickness Procedure set forth in the present description.

The surface area per volume (SA/V) terms used in the permeability equations for the various components are calculated using the surface area per volume expressions for either fibers or particles, as appropriate for the morphology of the individual component. For fibers, the surface area to volume ratio is equal to the perimeter to area ratio, p/a, of a cross-section taken perpendicular to the longitudinal axis of the cylinders. For a cylinder with a circular cross-section, for example:

$$SA/V = p/a = 2/r;$$

where r is the radius of the cylinder cross-section in cm.

For ribbon-like shapes; i.e., those with approximately rectangular cross-section:

$$SA/V = p/a = 2 \cdot (\text{width} + \text{thickness}/\text{width} \cdot \text{thickness})$$

For fibers with more complex cross-sectional shapes, the perimeter to area ratios can be determined by microscopic techniques well known in the art. For example, see E. E. Underwood, *Quantitative Stereology*, Addison Wesley Publishing Co. (1970). In these computations the surface area to volume ratio of substantially non-swelling fibers can be determined by using a "SA/V" value (for the fiber's surface area to volume ratio) which is appropriate to that fiber's cross-sectional shape. For example, fluff fibers are generally ribbon-like, with a rectangular cross-sectional shape. For a fluff fiber with a thickness of 8 microns (0.0008 cm) and a width of 40 microns (0.0040 cm), for example, the surface area per volume ratio is $$SA/V = p/a = 2 \cdot (8+40) \cdot 10^{-4} / ((8 \cdot 40) \cdot 10^{-8})$$

$$SA/V = 3000 \text{ cm}^{-1}$$

The superabsorbent morphology may be particulate, fibrous, flake-like or combinations thereof. Furthermore, superabsorbent swelling characteristics may be isotropic or anisotropic. The majority of the commercially available superabsorbents are in the form of particles which swell substantially isotropically. Such superabsorbent particles can be treated as spheres in the present computations. When the particle sizes are all substantially identical, the surface area to volume ratio for a sphere can be used to estimate the superabsorbents surface area to volume ratio. The surface area to volume ratio for a sphere is given by $$SA/V = 3/r$$

where r is the radius of the sphere in cm.

However, superabsorbent materials may be composed of a distribution of particle sizes. When this distribution is substantially monomodal, the count-weighted surface area to volume can be used. For a given distribution, this value can be calculated as follows:

$$\frac{SA}{V} = \frac{3 \cdot \sum_i (r_i^2 \cdot n_i)}{\sum_i (r_i^3 \cdot n_i)}$$

where
$r_i$ = mid point of the particle radius range of the $i^{th}$ portion, in cm.

$n_i$ = the number of particles within the $i^{th}$ portion $$n_i = m_i / [\rho_{SAP} \cdot (4/3) \cdot \pi \cdot r_i^3]$$

and
$m_i$ = mass fraction of particle within the $i^{th}$ portion in grams.
$\rho_{SAP}$ = density of the dry superabsorbent solid in g/cc.

If the particle size distribution is multi-modal, e.g. bi-modal, a separate permeability for each modal group should be used in the self-consistent calculation of the permeability of the composite material detailed below. In this instance, a count-weighted surface area to volume ratio should be calculated for each modal group, as described above. Typically, at least 6 to 8 different particle size fractions should be used to estimate the particle size distribution of the superabsorbent.

The swelling of the superabsorbent with the absorption of liquid further complicates the process of incorporating the contributions of the superabsorbent into the determination of the composite permeability. In particular, the size, and therefore surface area to volume ratio, of the superabsorbent will depend on the level of saturation of the superabsorbent. The relationship for the surface area to volume ratio of an isotropically swelling superabsorbent particle, as a function of its liquid content, is $$\left(\frac{SA}{V}\right)_{wet} = \frac{\left(\frac{SA}{V}\right)_{dry}}{\left[1 + \left(\frac{S \cdot \rho_{SAP}}{\rho_l}\right)\right]^{\left(\frac{1}{3}\right)}}$$

where
$(SA/V)_{wet}$ = surface area per volume ratio of the wet superabsorbent in cm$^{-1}$
$S$ = saturation of the superabsorbent expressed as grams of liquid per gram of superabsorbent
$\rho_{SAP}$ = density of the dry SAP in g/cc
$\rho_l$ = density of the liquid in g/cc
$(SA/V)_{dry}$ = surface area per volume ratio of the dry SAP in cm$^{-1}$ Superabsorbent materials may also be present in fibrous form. It has been observed that, in general, the fibrous superabsorbents will swell anisotropically. In particular, the increase in fiber volume with increased liquid content is primarily radial, with the fiber length remaining relatively constant. In such cases, the surface area to volume ratio of the swollen superabsorbent fiber is given by $$\left(\frac{SA}{V}\right)_{wet} = \frac{\left(\frac{SA}{V}\right)_{dry}}{\left[1 + \left(\frac{S \cdot \rho_{SAP}}{\rho_l}\right)\right]^{\left(\frac{1}{2}\right)}}$$

With the above relationships for surface area to volume ratio as a function of liquid content in the superabsorbent, the surface area to volume ratio for superabsorbent with a particular liquid content can be calculated. Before the surface area to volume ratio for each superabsorbent can be calculated for use in the permeability equations given above, the level of saturation of each superabsorbent in each layer should be determined. The following discussion describes the method used to estimate the level of saturation of each of the superabsorbents present in the absorbent core.

It has been observed that, in the time interval between delivery of the first and second liquid insults to the product, the liquid is essentially completely taken up by the superabsorbents in the system. Furthermore it has been observed that the liquid delivered during the first insult partitions between the superabsorbent materials in accordance with their relative amounts and liquid pickup rates. For the liquid loading specified above (0.6 g/cm²) the saturation, $S_j$, expressed as grams of liquid amount per gram of superabsorbent in each superabsorbent can be calculated as follows:

$$S_j = \frac{(f_{P_j} \cdot 0.6)}{(bw_j \cdot 10^{-4})}$$

$bw_j$=basis weight of the $j^{th}$ super absorbent in grams/square meter $f_{pj}$=liquid partition factor for the $j^{th}$ super absorbent Liquid partition factors, $f_{pj}$, are calculated for each superabsorbent component based on the relative rates and amounts of the various superabsorbent components.

$$f_{P_j} = \frac{f_{R_j} \cdot bw_j}{\sum_j (f_{R_j} \cdot bw_j)}$$

where $bw_j$=basis weight of the $j^{th}$ superabsorbent in grams/square meter $f_{Rj}$=the relative rate factor of the $j^{th}$ superabsorbent The relative rate factor, $f_{Rj}$, for each superabsorbent is given by $$f_{Rj} = \tau_1/\tau_j$$

where $\tau_j$=time required for the $j^{th}$ super absorbent to absorb 60% of its equilibrium capacity on the absorbency under no load (FAUZL) test described herein.

For purposes of illustrating the method, consider an example having a two layer absorbent with the following compositions:

Layer region 1:
  Superabsorbent type 1 of 400 micron count-weighted particle size at 120 gsm (grams per square meter), $\tau_1$=5 min, Wood pulp fluff at 120 gsm with 8 micron by 40 micron fiber cross-section, Measured thickness at the saturation level specified below=0.55 cm.

Layer region 2:
  Superabsorbent type 2 of 400 micron count-weighted particle size at 150 gsm, $\tau_2$=10 min, Wood pulp fluff at 300 gsm with 8 micron by 40 micron fiber cross-section, Measured thickness at the saturation level specified below=0.51 cm.

For the superabsorbents used in these layers $$f_{R1}=5/5=1$$

$$f_{R2}=5/10=0.5$$

and $$f_{P_1} = \frac{1 \cdot 120}{(1 \cdot 120 + 0.5 \cdot 150)} = 0.62$$

$$f_{P_2} = \frac{0.5 \cdot 150}{(1 \cdot 120 + 0.5 \cdot 150)} = 0.38$$

so that $$S_1 = \frac{(0.62 \cdot 0.6)}{(120 \cdot 10^{-4})} = 31 \frac{g}{g}$$

$$S_2 = \frac{(0.38 \cdot 0.6)}{(150 \cdot 10^{-4})} = 15.2 \frac{g}{g}$$

The above computations are appropriate when the total equilibrium FAUZL superabsorbent capacities are not exceeded at the specified loading of 0.6 g/cm². If the capacity of a particular superabsorbent material is exceeded under these circumstances, its saturation is set to the equilibrium value and the excess liquid is assumed to reside in the other superabsorbents in a manner consistent with the descriptions given herein.

Based on the amounts of liquid located within the superabsorbent particles, the surface area to volume ratio of the swollen particles or fibers in each layer can be calculated using the appropriate surface area to volume ratio equations given above for the swollen particles and/or fibers. The permeability equation identified for spheres should be used for the particulate superabsorbents, and the permeability equation identified for cylinders should be used for fibrous superabsorbents.

In this particular example the superabsorbents are in particulate form so their surface area to volume ratios when the core contains 0.6 g/cm² liquid are as follows.

Layer region 1 superabsorbent:

$$\left(\frac{SA}{V}\right)_{SAP\,1} = \frac{\left(\frac{SAV}{V}\right)_{dry}}{\left[1 + \left(\frac{S \cdot \rho_{SAP}}{\rho_l}\right)\right]^{1/3}}$$

$$= \frac{3/(200 \cdot 10^{-4})}{\left[1 + \left(\frac{31 \cdot 1.48}{1}\right)\right]^{(\frac{1}{3})}} = 41.6 \text{ cm}^{-1}$$

Layer region 2 superabsorbent:

$$\left(\frac{SA}{V}\right)_{SAP\,2} = \frac{\left(\frac{SAV}{V}\right)_{dry}}{\left[1 + \left(\frac{S \cdot \rho_{SAP}}{\rho_l}\right)\right]^{(\frac{1}{3})}}$$

$$= \frac{3/(200 \cdot 10^{-4})}{\left[1 + \left(\frac{15.2 \cdot 1.48}{1}\right)\right]^{(\frac{1}{3})}} = 52.4 \text{ cm}^{-1}$$

Fibrous woodpulp fluff component used in both layers:

$$SA/V = p/a = 2 \cdot (8+40) \cdot 10^{-4}/((8 \cdot 40) \cdot 10^{-8})$$

$$SA/V = 3000 \text{ cm}^{-1}$$

One can now set up appropriate equations for determining the permeability of each of the components within each composite layer region employed to construct the absorbent core by using the above expressions for the permeabilities of collections of fibers or collections of particles. However, the above-expressions for the permeabilities of the collections of fibers and/or particles are valid only if the entire porous medium consists solely of monodisperse fibers or particles. When both fibers and particles are present in a medium of specified porosity, the above expressions are combined. The method used to combine these two is in accordance the self-consistent method outlined in A. L. Berdichevsky and Z. Cai, "Preform Permeability Predictions by Self-consistent Method and Finite Element Simulation", *Polymer Composites*, 14(2), (1993).

For the present description, the basic premise behind the self-consistent method is that the permeability is substantially homogeneous throughout the porous medium. Therefore, the local porosity values corresponding to the fibers and the particles are determined such that their local permeabilities are equal. The above computation is subject to the constraint that the overall porosity ($\epsilon_{comp}$) of the structure be maintained at the specified value which is determined from the measured sample area and thickness, as described above. The simplest composite composition consists of two components. In this case, two permeability equations will be required for the self-consistent calculation of composite permeability. For the present two layer example described above the permeability equations to be used in the self-consistent composite permeability computation are as follows:

The permeability equations for layer 1 and layer 2 are:

Layer region 1:

fiber $K_{fiber\ 1} = \left(\dfrac{0.30}{(3000)^2}\right)(1-\epsilon_{fiber\ 1})\left(\dfrac{\epsilon_{fiber\ 1}}{1-\epsilon_{fiber\ 1}}\right)^{2.5}$ superabsorbent $K_{SAP\ 1} = \left(\dfrac{0.3555}{(41.6)^2}\right)(1-\epsilon_{SAP\ 1})\left(\dfrac{\epsilon_{SAP\ 1}}{1-\epsilon_{SAP\ 1}}\right)^{2.35}$ Layer region 2:

fiber $K_{fiber\ 2} = \left(\dfrac{0.30}{(3000)^2}\right)(1-\epsilon_{fiber\ 2})\left(\dfrac{\epsilon_{fiber\ 2}}{1-\epsilon_{fiber\ 2}}\right)^{2.5}$ superabsorbent $K_{SAP\ 2} = \left(\dfrac{0.3555}{(52.4)^2}\right)(1-\epsilon_{SAP\ 2})\left(\dfrac{\epsilon_{SAP\ 2}}{1-\epsilon_{SAP\ 2}}\right)^{2.35}$ where $\epsilon_{fiber1}$, $\epsilon_{SAP1}$, $\epsilon_{fiber2}$ and $\epsilon_{SAP2}$ correspond to the local porosity values of the fiber and superabsorbents in layers 1 and 2, respectively. The combination of the local porosities must yield the correct overall porosity obtained from thickness measurements described earlier, namely $$\epsilon_{comp} = 1 - \dfrac{bwt_{comp} \cdot 10^{-4} \cdot \left[\sum_k \left(\dfrac{f_k}{\rho_k}\right) + \sum_j \left(\dfrac{f_j}{\rho_j}\right) + \sum_j \left(\dfrac{S_j \cdot f_j}{\rho_l}\right)\right]}{h_{comp}}$$

where:

$bwt_{comp}$=basis weight of the composite in grams per square meter $f_k$=mass fraction of the composite provided by the $k^{th}$ fiber $f_j$=mass fraction of the composite provided by the $j^{th}$ superabsorbent such that $$\sum_k f_k + \sum_j f_j = 1$$

and $\rho_k$=density of the $k^{th}$ fiber, $\rho_j$=density of the $j^{th}$ superabsorbent, $\rho_l$=density of the liquid, $S_j$=level of saturation of the $j^{th}$ superabsorbent in grams liquid per gram of that superabsorbent, $h_{comp}$=thickness (cm) of the composite at the level of liquid loading equal to the total liquid load in the composite, where the total liquid load in the composite is given by:

$$bwt_{comp} \cdot 10^{-4} \cdot \sum_j (S_j \cdot f_j).$$

For the two layer example given above with only one type of fiber and one type of superabsorbent in each layer, the density of the fiber component in both layers is 1.5 g/cc, the density of the superabsorbent component in both layers is 1.48 g/cc and the superabsorbent mass fractions, liquid loadings, and composite heights of each layer are as specified above. The overall porosity values are as follows:

Layer region 1:

$\epsilon = 1 - \dfrac{240 \cdot 10^{-4}(0.5/1.5 + 0.5/1.48 + 31 \cdot 0.5)}{0.55} = 0.29$ Layer region 2:

$\epsilon = 1 - \dfrac{450 \cdot 10^{-4}(0.67/1.5 + 0.33/1.48 + 15.2 \cdot 0.33)}{0.51} = 0.50$ The values for the permeability of the two layers after conducting the self-consistent calculation are:

Layer Region 1:

$K=1.6 \cdot 10^{-6}$ cm$^2$

Layer region 2

$K=1.1 \cdot 10^{-6}$ cm$^2$

This simple two layer case serves to illustrate the principle composite permeability calculation. However, the composites used in constructing the absorbent core of this invention may include more than two components. In such instances, it is necessary to include a permeability equation for each component within a given composite layer region when executing the self-consistent composite permeability computation for that layer region. For example, if a composite layer region contains two fiber types and two superabsorbents, four permeability equations will be required in the computation of the composite permeability when employing the self-consistent method.

With the composite permeabilities and thicknesses (height, h) determined for each layer region of the absorbent core in its partially saturated state, as described above, it is now possible to calculate the Flow Conductance Value for the system. As described previously, Flow Conductance Value=$K_1h_1+K_2h_2+K_3h_3+\ldots$ So, for the two layer example given above:

Flow Conductance Value = $(1.6*10^{-6}*0.55)+(1.1*10^{-6}*0.51)$ $= 1.4*10^{-6}$ cm$^3$ While the above calculations of the permeability and flow conductance are illustrated for a two layer structure whose layers each contain one isotropically swelling particulate superabsorbent and one fiber type, the calculation of the flow conductance can be extended to cases including more than two layers, and the calculation of the permeability, K, can be readily adapted for more complex materials, in accordance with the description set forth herein.

Liquid Wicking Value

Scope

This test is used to determine the capability of an absorbent material to remove liquid from the target area.

Summary

Determine the amount of liquid to be applied to a sample based on the liquid partitioning calculations. Allow the sample to absorb the liquid from a reservoir and determine the amount of liquid that has been removed from the target area.

Equipment and Materials

A 21 cm by 21 cm piece of Plexiglas, or similar material, of 5 mm or less thickness.

Suitable liquid reservoir.

Lab balance.

A sample support for holding the absorbent sample vertical during the addition of liquid to the sample.

Binder clips for holding sample to the Plexiglas, such as Medium binder clip No. 10050 from IDL Corporation, Caristadt, N.J.

Laboratory oven at 150 degrees centigrade.

Test Materials

Test liquid, saline solution; Recommended Saline, Blood bank saline solution, such as Catalog No. 8504 Blood bank saline obtained from Stephens Scientific, a division of the Cornwell Corporation, a business having offices located at Riverdale, N.J.; or a substantial equivalent.

Sample Preparation

Remove the sample layer region from the product, or otherwise prepare a sample having the same shape as will exist in the product. Each layer should be separated and tested separately.

Mark the target location with a permanent ink marker. The target location of the layer being tested is determined when the layer is at its intended position in the absorbent core. The target location is at a laterally centered area which is located inboard from the terminal front edge of the furthest frontward extending absorbent layer of the absorbent core by a distance equal to 36% of the overall length of the absorbent core. Accordingly, the furthest frontward extending absorbent layer of the absorbent core is not necessarily the layer being tested.

Mark the target area on the sample with a permanent ink marker. The target area of the sample layer being tested is determined when the layer is at its intended position in the absorbent core. The target area of the test sample layer is the area of the sample layer which lies between two, laterally extending lines. The first line is positioned inboard from the terminal front edge of the furthest frontward extending absorbent layer of the absorbent core by a distance equal to 24% of the overall length of the absorbent core. The second line is positioned inboard from the terminal front edge of the furthest frontward extending absorbent layer of the absorbent core by a distance equal to 59% of the overall length of the absorbent core. Both lines are substantially perpendicular to the longitudinally extending centerline of the absorbent core. If both of these two target area lines fall outside the boundary edges of the absorbent sample being tested, then the Liquid Wicking Value of the sample being tested will be zero by definition.

Calculate the amount of liquid to be absorbed by the sample by using the liquid partitioning calculations, as set forth in the description for calculating the Flow Conductance Value. However, rather than calculating the SAP saturation for each layer, determine only the amount of liquid predicted to be within each layer. This can be done by using the following equation:

Liquid in Layer "j"=$(f_{pj})$*1.0 g/cm$^2$*Target Zone Surface Area.

(e.g., for the example given with the description of the determination of the Flow Conductance Value; 61.6 grams of liquid in layer region 1, and 38.4 grams of liquid in layer region 2, when employing a 100 cm$^2$ target zone surface area).

Set-up Procedure

Place the sample on the Plexiglas sample holder such that the target location is directly at the bottom of the apparatus.

Fill the liquid reservoir to a point approximately 1 cm from the top.

Place the reservoir on the lab balance.

Test Procedure

Tare the balance.

Suspend the sample in the reservoir such that the liquid touches the absorbent system. Fluid contact must be maintained throughout the procedure.

Using the lab balance as a reference, allow the absorbent composite to absorb the quantity of fluid determined in the previous calculations. Remove the sample from the reservoir when the sample has absorbed an amount equal to that based on fluid partitioning calculations±5 gms.

Allow the sample to remain undisturbed for five minutes in the vertical position.

Cut the sample at the target area marks and remove the center portion. Weigh the remaining sections.

Dry the remaining sections in an oven overnight.

Weigh the dry samples and subtract this weight from the wet weight to determine the amount of liquid which moved out from the target area. Divide the amount of liquid removed from the target area (i.e. the amount measured by the previous step) by the total amount of liquid applied to the target area (e.g. target zone surface area in cm$^2$, multiplied by 1 g of liquid per cm$^2$); and multiply that result by 100. This is the Liquid Wicking Value of the layer region.

The Liquid Wicking Value of a multi-layer absorbent composite is the largest Liquid Wicking Value provided any one of the layers. For example, the Liquid Wicking Value of a two-layer, absorbent composite is the larger of the two Liquid Wicking Values provided by the two layers.

Combined Conductance-Wicking Value (C)

The Combined Conductance-Wicking Value can be determined in accordance with the following formula:

$$C = (FCV) + \frac{(LWV)}{(3 \cdot 10^6)}$$

where:

FCV=Flow Conductance Value in units of cm$^3$;

LWV=Liquid Wicking Value in percent; and $(3 \cdot 10^6)$ has the units of cm$^{-3}$.

Modified Absorbency Under Load (MAUL)

Scope

This test is designed to measure the ability of a particulate superabsorbent polymer (SAP) to absorb saline while under a constant load of 0.3 psi (2.07 KPa). More specifically, the test measures the amount of saline absorbed by 0.160 grams of superabsorbent polymer, which has been prescreened through a U.S. std. #30 mesh and retained on a U.S. std. #50 mesh., when it is confined within a 5.07 $cm^2$ area under a pressure of 0.3 psi (2.07 KPa). A suitable testing device is representatively shown in FIGS. 10 through 14.

Equipment and Materials

Electronic balance, accurate to 0.001 gram (200 gram minimum capacity).

Cylinder group: 1 inch (25.4 mm) inside diameter, plastic cylinder (120) with a 100 mesh stainless steel screen affixed to the cylinder bottom; 4.4 gram plastic piston disk (122) with a 0.995 inch (25.27 mm) diameter. The piston disk diameter is 0.005 inch (0.13 mm) smaller than the inside diameter of the cylinder. See FIG. 11.

100 gram weight (124) having a 0.984 inch (25 mm) diameter.

0.9% (wt/wt) NaCl solution (Blood Bank Saline).

Saline basin (126).

Timer (140) capable of reading 200 minutes at one second intervals. Weighing paper.

U.S. Standard Testing Sieve (A.S.T.M. E-11 Specification) grouping including one receiver, one U.S. std. #30 mesh, one U.S. std. #50 mesh, and one lid.

Figure 10:
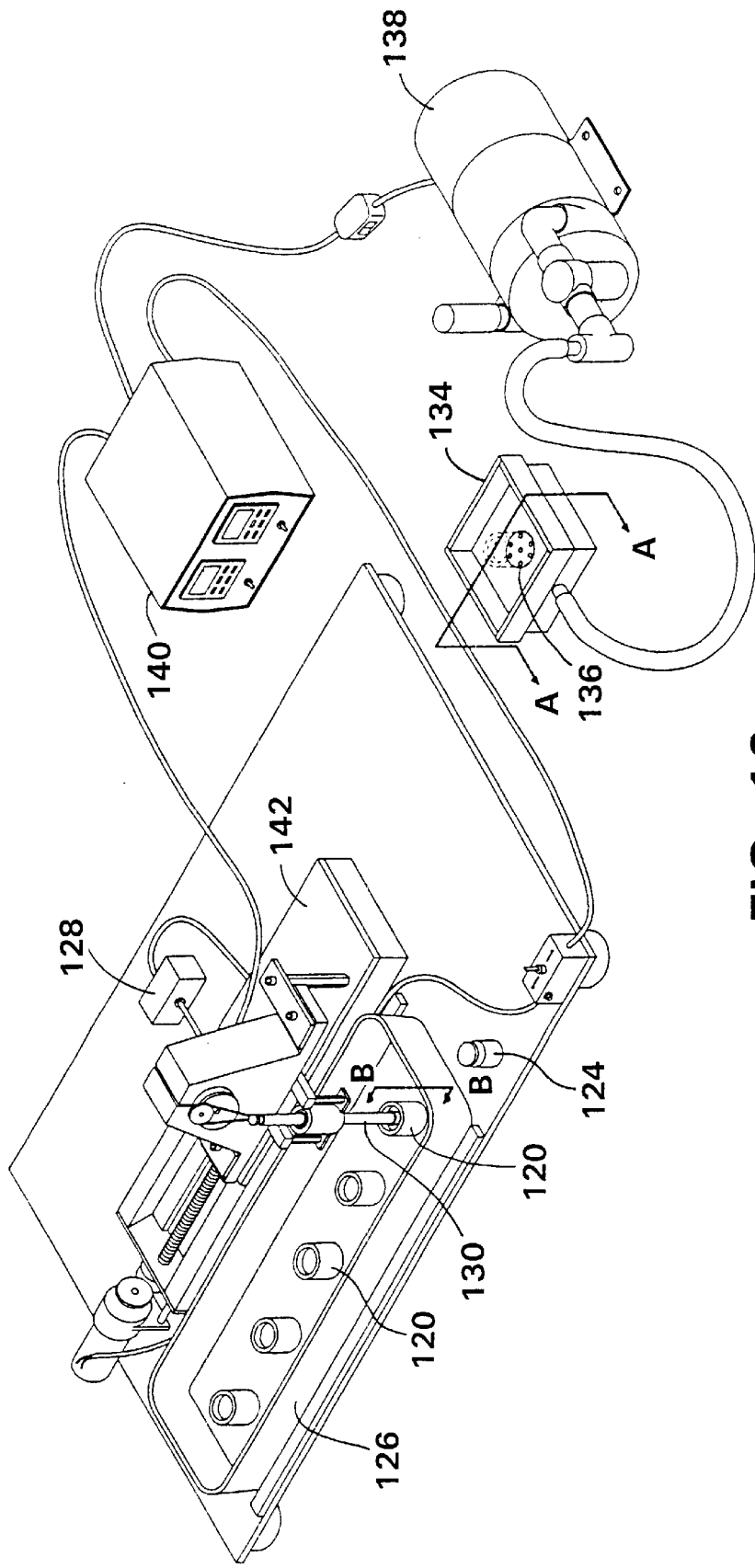
FIG. 10 shows a schematic representation of a testing apparatus for determining particular properties of a superabsorbent material.
Figure 12:
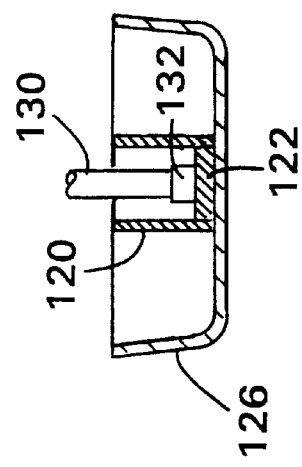
FIG. 12 shows a representative cross-sectional view of a cylinder group placed in a basin with a piston rod positioned for tapping against a piston disk.

A tapping device is positioned above the sample to provide a consistent tapping onto the supporting piston disk, as illustrated in FIGS. 10 and 12. This tapping dislodges any trapped air surrounding the SAP and ensures that liquid wets the SAP surface. In this setup, a motor (128) rotates a shaft which drives a rod (130) along an up and down stroke. At the lower end of the rod is a rubber foot (132) which has a diameter of 13 mm, as illustrated in FIG. 12. The shaft stroke is 3 cm and it completes a full up and down stroke cycle every 0.7 seconds. The maximum pressure that the piston disk will apply to the SAP at impact is 0.16 psi (0.11 KPa).

With reference to FIG. 10, a fixture (134) has a vacuum port (136) that allows for the evacuation of interstitial liquid from the sample. The port accommodates the base of the cylinder group. When the cylinder group containing the sample is placed on the fixture, the free liquid is removed from between the sample particles. A suitable pump (138) applies a vacuum pressure applied to the sample of 100 torr (13.3 KPa) or less.

FIG. 10 shows the entire test setup. It should be noted that electronic timers (140) are desirably employed to control the duration of the tapping and vacuum devices. In this setup the tapping device also rests onto a slide (142) which would allow movement between multiple samples.

Procedure

Figure 13:
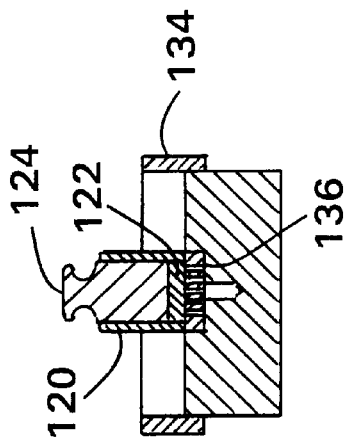
FIG. 13 shows a representative cross-sectional view of a cylinder group with a weight applied onto a piston disk, and placed on a vacuum fixture.
Figure 11:
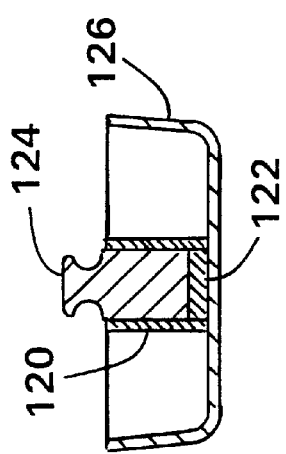
FIG. 11 shows a representative cross-sectional view of a cylinder group placed in a basin with a weight applied onto a piston disk.

1. Using the U.S.A. Standard Testing Sieve grouping, sieve enough superabsorbent to provide a minimum of 0.160 grams that passes through the #30 mesh screen and is retained on the #50 mesh screen.
2. Weigh out 0.160 grams ( 0.001 grams) of sieved superabsorbent from step 1 onto the pre-tared weighing paper.
3. Slowly pour the superabsorbent into the cylinder having the 100 mesh bottom. Avoid allowing the SAP to contact the sides of the cylinder because granules may adhere. Gently tap the cylinder until the granules are evenly distributed on the screen.
4. Place the plastic piston in the cylinder. Weigh this cylinder group and record the weight as the "cylinder group superabsorbent amount."
5. Fill the saline basin to a 1 cm height with the blood bank saline.
6. Place the cylinder group in the saline basin, directly below the shaft of the tapping device and start the timer. Start the tapping device to tap for an eight second period.
7. Within 5 seconds of the end of the eight second tapping period, place the 100 g weight on top of the cylinder group piston, as illustrated in FIG. 11.
8. 200 minutes after the cylinder is placed into the basin, remove the cylinder group and weight, place the cylinder group and 100 g weight onto the vacuum platform, as illustrated in FIG. 13. Apply the vacuum for a 6 second period.
9. Remove the 100 gram weight from the cylinder group, weigh the cylinder group, and record the weight.

Results and Analysis

For each test, calculate the grams of saline absorbed per gram of SAP. This is the MAUL value for the superabsorbent.

Flooded Absorbency Under Zero Load (FAUZL)

Scope

This test is designed to measure the saline absorption rate of particulate superabsorbent polymer (SAP). The test measures, as a function of time, the amount of saline absorbed by 0.160 grams of superabsorbent polymer (starting either dry or presaturated) when it is confined within a 5.07 $cm^2$ area under a determined nominal pressure of 0.01 psi (0.069 KPa). From the resulting absorption versus time data, the characteristic time (Tau) to reach 60% of the equilibrium absorption capacity is determined.

Equipment & Materials

Electronic balance, accurate to 0.001 gram (200 gram minimum capacity).

Cylinder group: 1 inch (25.4 mm) inside diameter, plastic cylinder (120) with a 100 mesh stainless steel screen affixed to the cylinder bottom; 4.4 gram plastic piston disk (122) with a 0.995 inch (25.27 mm) diameter. The piston disk diameter is 0.005 inch (0.13 mm) smaller than the inside diameter of the cylinder. See FIG. 11.

0.9% (wt/wt) NaCl solution (Blood Bank Saline).

Saline basin.

Timer (140) capable of reading 120 minutes at one second intervals.

Weighing paper.

A tapping device is positioned above the sample to provide a consistent tapping onto the supporting piston disk, as illustrated in FIGS. 10 and 12. This tapping dislodges any trapped air surrounding the SAP and ensures that liquid wets the SAP surface. In this setup, a motor (128) rotates a shaft which drives a rod (130) along an up and down stroke. At the lower end of the rod is a rubber foot (132) which has a diameter of 13 mm, as illustrated in FIG. 12. The shaft stroke is 3 cm and it completes a full up and down stroke cycle every 0.7 seconds. The maximum pressure that the piston disk will apply to the SAP at impact is 0.16 psi (0.11 KPa).

With reference to FIG. 10, a fixture (134) has a vacuum port (136) that allows for the evacuation of interstitial liquid from the sample. The port accommodates the base of the cylinder group. When the cylinder group containing the sample is placed on the fixture, the free liquid is removed from between the sample particles. A suitable pump (138) applies a vacuum pressure applied to the sample of 100 torr (13.3 KPa) or less.

FIG. 10 shows the entire test setup. It should be noted that electronic timers (140) are desirably employed to control the duration of the tapping and vacuum devices. In this setup the tapping device also rests onto a slide (142) which would allow movement between multiple samples.

Procedure

Figure 14:
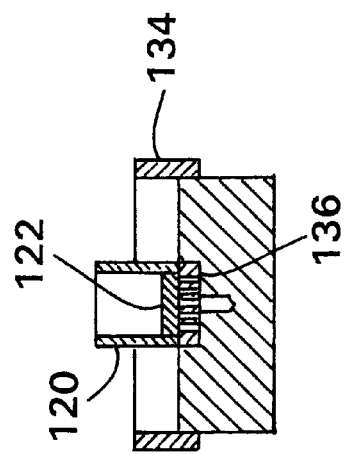
FIG. 14 shows a representative cross-sectional view of a cylinder group placed on a vacuum fixture.

1. Weigh out 0.160 grams (±0.001 grams) of superabsorbent onto the pre-tared weighing paper. The particle size distribution is the "as received" particle size distribution.
2. Slowly pour the superabsorbent into the cylinder having the 100 mesh bottom. Avoid allowing the SAP to contact the sides of the cylinder because granules may adhere. Gently tap the cylinder until the granules are evenly distributed on the screen.
3. Place the plastic piston in the cylinder. Weigh this cylinder group and record the weight as the "cylinder group superabsorbent amount."
4. Fill the saline basin to a 1 cm height with the blood bank saline.
5. Place the cylinder group in the saline basin, directly below the shaft of the tapping device and start the timer. Start and operate the tapping device to tap for an eight second cycle.
6. Five minutes after the cylinder is placed into the basin, remove the cylinder, stop the timer and place the cylinder onto the vacuum platform, as illustrated in FIG. 14. Apply the vacuum for a 6 second period.
7. Weigh the cylinder group and record the weight.
8. Return the cylinder group to the basin below the tapping device and again start the timer. Note that the time between removing the cylinder group from the saline in step 6 to reintroducing the cylinder group to the saline in step 8 should not exceed 30 seconds. Repeat the initial sequence of soaking, removing, vacuuming, and weighing to gather and record data at cumulative soak times of 1, 5, 10, 15, 30, 45, 60, 75, 90 and 120 minutes.
9. Conduct the procedure described in steps 1–8 a total of three times.

Results and Analysis

Calculate the grams of saline absorbed per gram of superabsorbent polymer, and plot as a function of cumulative soak time.

Determine the final equilibrium absorption capacity of the SAP: If there is less than a 5% change in the average capacity (average of three tests) of the SAP obtained at 90 and 120 minutes, then use the capacity at 120 minutes as the equilibrium capacity, FAUZL. If there is greater than a 5% change in the average capacity, then the sample testing will need to be repeated and will need to include an additional sampling at a cumulative soak time of 200 minutes. Use the capacity at 200 minutes as the equilibrium capacity, FAUZL, for this latter situation.

Determine the interpolated time (Tau) to reach 60% of the equilibrium absorption capacity. This is done by calculating the capacity at 60% of the equilibrium value, then estimating the correspond time to reach this capacity from the graph. The interpolated time to reach 60% capacity (by this procedure), is obtained by performing a linear interpolation with the data points that lay to either side of the estimated time.

Calculate the arithmetic average interpolated time to reach 60% of the equilibrium capacity (average of three tests). This average time value is referred to as "Tau" ($\tau$).

Liquid Contact Angle with Fibers

A suitable technique for measuring the liquid contact angle with a fiber is described in U.S. Pat. No. 5,364,382, the entire disclosure of which is incorporated herein by reference in a manner that is consistent herewith. In particular, the wettability of fibers can be determined using contact angle measurements on fibers. Repeat cycle, single fiber contact angle measurements using distilled water can be performed with a Cahn Surface Force Analyzer (SFA222) and WET-TEK data analysis software. The SFA222 is available from Cahn Instruments, Inc., of Cerritos, Calif., and the WET-TEK software is available from Biomaterials International, Inc., of Salt Lake City, Utah. Fibers are tested through three measurement cycles, and the bath of distilled water is changed between cycles one and two. The liquid contact angle for the fiber material is determined by taking the arithmetic average of the three measurements. The test instrument is operated in accordance with the standard operating techniques described in the Cahn SFA-222 System Instruction Manual supplied by the manufacturer.

EXAMPLES

The following Examples are presented to provide a more detailed understanding of the invention, and are not intended to limit the scope of the invention. In the various examples, it should be noted that the first primary layer portion 48 may alternatively be referred to as the top layer or upper layer, and that the second primary layer portion 50 may alternatively be referred to as the bottom layer or lower layer.

Example 1

The bodyside layer is at a basis weight of 500 gsm and is composed of 50% 53C superabsorbent, a superabsorbent available from Dow Chemical, and 50% HPF2 mercerized pulp, a material available from Buckeye Corp. The Dow 53C superabsorbent has a $\tau$ of 8.5 minutes; a FAUZL capacity of 33 g/g; and a 0.3 psi MAUL value of 26.2 g/g. The bodyside layer extends over the area of the layer 48 shown in FIG. 2, and is densified to 0.2 g/cc.

The outer side layer is composed of three layers of 68 gsm uncreped through air dried tissue, composed of 50% HPZ fibers available from Buckeye Cellulose Corp, and 50% LL1 9 fibers available from Kimberly-Clark Company extending over the entire pad area (the area of layer 50). A 50 gsm layer of SXM 880 superabsorbent, available from Stockhausen, is placed between the outermost layer of tissue and the adjacent tissue, using 10 gsm of adhesive. The SXM 880 superabsorbent has a $\tau$ of 4 minutes; a FAUZL capacity of 38 g/g; and a 0.3 psi MAUL value of 29.8 g/g. Two additional sheets of uncreped through air dried tissue as described previously are placed in the areas outside of the area occupied by the body side layer 48. Between these two layers is a layer of 100 gsm SXM 880 superabsorbent, bound using 10 gsm of the previously mentioned adhesive.

This example has a Flow Conductance Value of $3.56 \times 10^{-6}$ and a Liquid Wicking Value of 56.2%.

Example 2

The bodyside layer is at a basis weight of 500 gsm and is composed of 50% 53C superabsorbent, a superabsorbent available from Dow Chemical, and 50% HPF2 mercerized pulp, a material available from Buckeye Crop. The Dow 53C superabsorbent has a τ of 8.5 minutes; a FAUZL capacity of 33 g/g; and a 0.3 psi MAUL value of 26.2 g/g. The bodyside layer extends over the area of the layer region 48, as shown in FIG. 2, and is densified to 0.2 g/cc.

The outer side layer is composed of 4 layers of 68 gsm uncreped through air dried tissue composed of 50% HPZ fiber from Buckeye Cellulose and 50% LL19 fiber available from Kimberly-Clark Company. SXM 880 superabsorbent, available from Stockhausen, is distributed such that it has a basis weight of 50 gsm in the area under the body side layer and a basis weight of 150 gsm in areas outside of this. Superabsorbent extends over the entire area of the pad (the area of layer 50). The SXM 880 superabsorbent has a τ of 4 minutes; a FAUZL capacity of 38 g/g; and a 0.3 psi MAUL value of 29.8 g/g. The superabsorbent is sandwiched between the $2^{nd}$ and $3^{rd}$ outer most layers of tissue.

This example has a Flow Conductance Value of $3.56 \times 10^{-6}$ and a Liquid Wicking Value of 50.0%.

The above data can be summarized as follows:

| Example # | Flow Conductance Value($\times 10^6$) | Liquid Wicking Value(%) | Combined Conductance-Wicking Value ($\times 10^{-6}$ cm$^3$) |
|---|---|---|---|
| 1 | 3.30 | 56.2 | 22.0 |
| 2 | 3.56 | 50.0 | 20.2 |

Some conventional absorbent structures have identified the need for improved distribution, and other conventional structures have identified the need for improved intake. Such conventional structures, however, have not been configured to provide the distinctive combination of liquid intake and distribution provided by the various arrangements and aspects of the present invention. The following comparative Examples 4 through 8 were prepared.

| Example # | Upper Layer SAP Type SAP BW | Upper Layer Fluff Type Fluff BW | Lower Layer SAP Type SAP BW | Lower Layer Fluff Type Fluff BW |
|---|---|---|---|---|
| Example 4[A] | SXM 880 215 gsm | CR -1654 400 gsm | SXM 880 78 gsm | CR -1654 232 gsm |
| Example 5[B] | 20/30 SXM 870 269 gsm | CCLC 292 gsm | 60/100 SXM 870 529 gsm | CCLC 294 gsm |
| Example 6[B] | SXM 870 159 gsm | CCLC 295 gsm | 601100 SXM 870 319 gsm | CCLC 295 gsm |
| Example 7[B] | 20130 SXM 870 99 gsm | CCLC 281 gsm | 60/100 SXM 870 239 gsm | CCLC 281 gsm |
| Example 8[C] | N/A | CCLC 300 gsm | SXM 880 250 gsm | CR -1654 250 gsm |

[A]It is believed that Example 4 is representative of the structure taught by USP 5,356,403 to Faulks, et al. In Example 4, the upper layer had a density of 0.2 g/cc, and the lower layer had a density of 0.3 g/cc.
[B]It is believed that Examples 5 through 7 are representative of the structures taught by EP 0 631 768 A1 of Plischke, et al.. In these examples, both layers had a density of 0.2 g/cc and both layers extended over the full area of the composite pad shape described in EP 0 631 768 Al.
[C]It is believed that Example 8 is representative of the structure taught by USP 5,360,420 to Cook, et al. The top layer had a density of 0.07 g/cc, and the bottom layer had a density of 0.25 glcc. Both layers had the shape described in USP 5,360,420.

CCLC is chemically cross-linked cellulose, as described in U.S. Pat. No. 4,898,642, for example.

SXM 870 and SXM 880 are superabsorbents produced by Stockhausen under the tradename FAVOR SX. Where indicated, the superabsorbent is sieved to the listed particle size in mesh; e.g. 20/30 mesh (600 to 850 μm), 60/100 mesh (150 to 250 μm).

The SXM 880 superabsorbent has a τ of 4 minutes; a FAUZL capacity of 38 g/g; and a 0.3 psi MAUL value of 29.8 g/g.

The SXM 870 superabsorbent has a τ of 4 minutes; a FAUZL capacity of 32.5 g/g; and a 0.3 psi MAUL value of 27 g/g.

The "20/30 SXM 870" superabsorbent has a τ of 6.4 minutes; a FAUZL capacity of 34 g/g; and a 0.3 psi MAUL value of 28.8 g/g.

The "60/100 SXM 870" superabsorbent has a τ of 3.3 minutes; a FAUZL capacity of 27.5 g/g; and a 0.3 psi MAUL value of 25.3 g/g.

Examples 4–8 exhibited the characteristics set forth in the following Table.

| Example | Flow Conductance Value ($\times 10^{-6}$ cm$^3$) | Liquid Wicking Value (%) | Combined Conductance-Wicking Value ($\times 10^{-6}$ cm$^3$) |
|---|---|---|---|
| 4 | 2.9 | 31.7 | 13.5 |
| 5 | 6.75 | 13.3 | 11.2 |
| 6 | 6.75 | 13.4 | 11.2 |
| 7 | 6.68 | 20.8 | 13.6 |
| 8 | 1.4 | 35.2 | 13.1 |

As can be seen, the structures of these examples do not provide the combination of characteristics afforded by the structures of the present invention.

Examples 9–10

For Examples 9 and 10, two-layer absorbent composite structures were constructed in accordance with the following Table:

| | |
|---|---|
| Upper Layer: | 200 g/m$^2$ of Stockhausen W52521 superabsorbent; and 133 g/m$^2$ of woodpulp fluff. |
| Lower Layer: | 239 g/m$^2$ of Stockhausen Favor 870 superabsorbent; and 281 g/m$^2$ of woodpulp fluff. |

The woodpulp fluff set forth in Table 1 had the designation CR-1654, which is available from Alliance Forest Products, a company located in Coosa Pines, Ala.

In both layers, the superabsorbent was uniformly mixed with the woodpulp fluff. Both the upper layer and lower layer had a density of 0.2 g/cm$^3$, and both layers extended over the entire composite pad. The composite pad employed the pad shapes described in EP 0 631 768 of Plischke, et al.

In Example 9, the Stockhausen W52521 superabsorbent was employed in its as-received condition, as supplied by Stockhausen, Inc. The as-received W52521 superabsorbent had a τ value of 4 minutes.

The two-layer absorbent structure constructed for Example 9 had the following properties:

Upper Layer with W52521 superabsorbent material; Liquid wicking value=1.4%.

Lower Layer with 870 superabsorbent material; Liquid wicking value=13.3%.

Accordingly, the Liquid Wicking value for the two-layer composite was the 13.3%.

In Example 10, the Stockhausen W52521 superabsorbent was sieved employing U.S. Standard Testing Sieves, and the sieved superabsorbent had a resulting size fraction of 500–710 microns. The sieved W52521 superabsorbent had a τ value of 6.8 minutes.

The two-layer absorbent structure constructed in Example 10 had the following properties:

Upper Layer with W52521 superabsorbent material (500–710 micron, particle size); Liquid wicking value= 0.9%.

Lower Layer with 870 superabsorbent material; Liquid wicking value=9.9%.

Accordingly, the Liquid Wicking value for the two-layer composite was the 9.9%.

As can be seen, the structures of Examples 9 and 10 do not provide the properties afforded by the structures of the present invention.

Having described the invention in rather full detail, it will be readily apparent that various changes and modifications can be made without departing from the spirit of the invention. All of such changes and modifications are contemplated as being within the scope of the invention.

We claim:

1. An absorbent article, comprising:
   a backsheet layer,
   a substantially liquid permeable topsheet layer,
   an absorbent composite structure sandwiched between said backsheet and topsheet layers, said absorbent composite including an absorbent core having a first primary layer region and at least a second primary layer region;
   said second primary layer region having a selectively zoned, non-uniform basis weight;
   at least one of said first and second primary layer regions including a plurality of sublayers;
   at least one of said first and second primary layer regions having a Liquid Wicking Value of at least about 38%: and
   at least one of said primary layer regions including a superabsorbent material which exhibits a Tau value of not less than about 0.8 min.

2. An article as recited in claim 1, wherein said absorbent core has a dry thickness of not more than about 6 mm, and a minimum crotch width of not more than about 10 cm.

3. An article as recited in claim 1, wherein said article is configured for use by an adult, and wherein said absorbent core has a dry thickness of not more than about 6 mm, and a minimum crotch width of not more than about 14 cm.

4. An article as recited in claim 1, wherein said absorbent core has a Combined Conductance-Wicking Value of at least about $14*10^{-6}$ cm$^3$.

5. An article as recited in claim 4, wherein said absorbent core has a dry thickness of not more than about 6 mm and a minimum crotch width of not more than about 10 cm.

6. An article as recited in claim 1, wherein said first primary layer region is located on a bodyside of the absorbent composite, and said second primary layer region is located relatively outward from said first layer region.

7. An absorbent article as recited in claim 1, wherein at least one of said primary layer regions includes a superabsorbent material having a Modified Absorbency Under Load value of at least about 20 g/g.

8. An absorbent article which includes an absorbent core having a first primary layer region and at least a second primary layer region; wherein
   said second primary layer region having a selectively zoned, non-uniform basis weight;
   said second primary layer region includes a heterogeneous plurality of sublayers;
   said absorbent core has a longitudinal length, a lateral width and an appointed front-most edge;
   said first primary layer region has a basis weight of not less than about 100 g/m$^2$ and not more than about 700 g/m$^2$,
   said first primary layer region has a first layer region density of not less than about 0.03 g/cm$^3$ and not more than about 0.4 g/cm$^3$;
   said first primary layer region includes fibrous material in an amount which is not less than about 25 wt % and is not more than about 80 wt %;
   said fibrous material includes fibers having fiber sizes which are not less than about 4 μm and not more than about 20 μm;
   said first primary layer region includes a superabsorbent material in an amount which is not less than about 50 wt % and is not more than about 80 wt %;
   said superabsorbent material includes superabsorbent particles having particle sizes which are not less than about 110 μm and are not more than about 1000 μm;
   said superabsorbent material has an MAUL value of not less than about 20 g/g; and
   said superabsorbent material has a Tau value of not less than about 0.8 min.

9. An article as recited in claim 8, wherein said first primary layer region is substantially coterminous with side edges of said second primary layer region; and
   said first primary layer region contained within a zone which begins at a laterally extending line positioned about 7% of the core length inboard from said front-most edge of the absorbent core and extends to a laterally extending line positioned about 62% of the core length inboard from said front-most edge of the absorbent core.

10. An article as recited in claim 9, wherein said first primary layer region includes a binder material.

11. An article as recited in claim 8, wherein said second primary layer region includes a plurality of sublayers having uncreped-through-air-dried material.

12. An article as recited in claim 8, wherein said second primary layer region has a longitudinal extent which is greater than a longitudinal extent of said first primary layer region; and said second primary layer region has a lateral extent which is substantially coterminous with said first primary layer region.

13. An article as recited in claim 8, wherein said second primary layer region has a longitudinal extent which is greater than a longitudinal extent of said first primary layer region;
   said second primary layer region has a lateral extent which is less than a lateral extent of said first primary layer region; and
   a lateral extent of at least a portion of said second primary layer region is not less than about 30% of a lateral extent of a correspondingly adjacent portion of said first primary layer region.

14. An article as recited in claim 8, wherein said second primary layer region has a longitudinal extent which is greater than a longitudinal extent of said first primary layer region;
   said second primary layer region has a lateral extent which is greater than a lateral extent of said first primary layer region;
   a lateral extent of at least a portion of said first primary layer region is not less than about 30% of a lateral extent of a correspondingly adjacent portion of said second primary layer region.

15. An article as recited in claim 8, wherein a target area of said second primary layer region has a basis weight which is lower than a basis weight of non-target portions of said second primary layer region.

16. An article as recited in claim 8, wherein the target area of said second primary layer region has a basis weight which is not less than about 100 g/m² and is not more than about 250 g/m²; and a non-target portion of said second primary layer region has a basis weight which is not less than about 450 g/m² and is not more than about 550 g/m².

17. An article as recited in claim 16, wherein said second primary layer region has a second layer region density of not less than about 0.1 g/cm³ and not more than about 0.3 g/cm³;

said second primary layer region includes fibrous material in an amount which is not less than about 50 wt % and is not more than about 95 wt %;

said fibrous material includes fibers having fiber diameters which are not less than about 4 $\mu$m and not more than about 20 gm;

said fibrous material includes fibers which exhibit a water contact angle of not more than about 70 degrees;

said second primary layer region includes a superabsorbent material in an amount which is not less than about 5 wt % and is not more than about 50 wt %; and said superabsorbent material includes superabsorbent particles having dry particle sizes which are not less than about 110 $\mu$m, and are not more than about 1000 $\mu$m.

18. An article as recited in claim 17, wherein said superabsorbent material in said second primary layer region has a MAUL value of not less than about 20 g/g, and has a Tau value of at least about 0.4 minutes.

19. An article as recited in claim 18, wherein said superabsorbent material in said second primary layer region is configured as a superabsorbent layer laminated between layers of uncreped-through-air-dried material.

20. An article as recited in claim 19, wherein said article further comprises a backsheet layer and a substantially liquid permeable topsheet layer which are configured with said absorbent core sandwiched therebetween.

21. An article as recited in claim 20, wherein said absorbent core has a Flow Conductance Value of at least about $7*10^{-6}$ cm³; and at least one of said first and second primary layer regions has a Liquid Wicking Value of at least about 16%.

22. An article as recited in claim 21, wherein at least one of said first and second primary layer regions has a Liquid Wicking Value of at least about 36%.

* * * * *

UNITED STATES PATENT AND TRADEMARK OFFICE
CERTIFICATE OF CORRECTION

PATENT NO. : 6,437,214 B1
DATED : August 20, 2002
INVENTOR(S) : Rob David Everett et al.

It is certified that error appears in the above-identified patent and that said Letters Patent is hereby corrected as shown below:

Column 1,
Line 4, insert -- This application is a continuation-in-part application claiming the benefit of application serial number 09/097,029 entitled LAYERED ABSORBENT STRUCTURE WITH A ZONED BASIS WEIGHT AND A HETEROGENEOUS LAYER REGION and filed in the U.S. Patent and Trademark Office on June 12, 1999. The entirety of application serial number 09/097,029, is hereby incorporated by reference. --.

Signed and Sealed this

Eighteenth Day of October, 2005

JON W. DUDAS
*Director of the United States Patent and Trademark Office*